(12) United States Patent
Wang et al.

(10) Patent No.: US 11,184,976 B2
(45) Date of Patent: Nov. 23, 2021

(54) HYPERELASTIC BINDER FOR PRINTED, STRETCHABLE ELECTRONICS

(71) Applicant: The Regents of the University of California, Oakland, CA (US)

(72) Inventors: Joseph Wang, San Diego, CA (US); Rajan Kumar, La Jolla, CA (US); Ying Shirley Meng, San Diego, CA (US); Jae Wook Shin, La Jolla, CA (US); Lu Yin, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 320 days.

(21) Appl. No.: 16/189,701

(22) Filed: Nov. 13, 2018

(65) Prior Publication Data
US 2019/0159337 A1    May 23, 2019

Related U.S. Application Data

(63) Continuation of application No. 15/820,284, filed on Nov. 21, 2017, now Pat. No. 10,143,081.
(Continued)

(51) Int. Cl.
*H05K 1/00* (2006.01)
*H05K 1/02* (2006.01)
(Continued)

(52) U.S. Cl.
CPC ......... *H05K 1/0283* (2013.01); *A61B 5/1477* (2013.01); *C08F 297/046* (2013.01);
(Continued)

(58) Field of Classification Search
CPC ................ H05K 1/0283; H05K 2201/0133
(Continued)

(56) References Cited

U.S. PATENT DOCUMENTS 6,410,666 B1   6/2002  Grubbs et al.
9,502,734 B1   11/2016 Lim et al.
(Continued)

FOREIGN PATENT DOCUMENTS

WO    2017079445 A1    5/2017

OTHER PUBLICATIONS

Park et al., "Highly stretchable electric circuits from a composite material of silver nanoparticles and elastomeric fibres", Nature Nanotechnology, 2012, pp. 803-809.
(Continued)

*Primary Examiner* — Binh B Tran
(74) *Attorney, Agent, or Firm* — Perkins Coie LLP

(57) ABSTRACT

Disclosed are compositions, devices, systems and fabrication methods for stretchable composite materials and stretchable electronics devices. In some aspects, an elastic composite material for a stretchable electronics device includes a first material having a particular electrical, mechanical or optical property; and a multi-block copolymer configured to form a hyperelastic binder that creates contact between the first material and the multi-block copolymer, in which the elastic composite material is structured to stretch at least 500% in at least one direction of the material and to exhibit the particular electrical, mechanical or optical property imparted from the first material. In some aspects, the stretchable electronics device includes a stretchable battery, biofuel cell, sensor, supercapacitor or other device able to be mounted to skin, clothing or other surface of a user or object.

20 Claims, 18 Drawing Sheets

Related U.S. Application Data

(60) Provisional application No. 62/425,036, filed on Nov. 21, 2016.

(51) Int. Cl.

| | |
|---|---|
| C08L 53/02 | (2006.01) |
| A61B 5/1477 | (2006.01) |
| H01M 4/38 | (2006.01) |
| H01M 4/48 | (2010.01) |
| H01M 4/62 | (2006.01) |
| H01M 4/66 | (2006.01) |
| H01M 10/24 | (2006.01) |
| C08F 297/04 | (2006.01) |
| H05K 1/03 | (2006.01) |
| H05K 1/11 | (2006.01) |
| H05K 1/16 | (2006.01) |
| H05K 3/32 | (2006.01) |
| C01B 32/158 | (2017.01) |
| A61B 5/1486 | (2006.01) |
| A61F 13/49 | (2006.01) |
| H01M 10/0565 | (2010.01) |

(52) U.S. Cl.
CPC .............. *C08L 53/02* (2013.01); *H01M 4/38* (2013.01); *H01M 4/48* (2013.01); *H01M 4/622* (2013.01); *H01M 4/663* (2013.01); *H01M 4/666* (2013.01); *H01M 4/668* (2013.01); *H01M 10/24* (2013.01); *H05K 1/028* (2013.01); *H05K 1/0393* (2013.01); *H05K 1/118* (2013.01); *H05K 1/16* (2013.01); *H05K 3/326* (2013.01); *A61B 5/14865* (2013.01); *A61B 2562/164* (2013.01); *A61B 2562/166* (2013.01); *A61F 13/4902* (2013.01); *C01B 32/158* (2017.08); *H01M 10/0565* (2013.01); *H05K 2201/0133* (2013.01)

(58) Field of Classification Search
USPC .................................................. 361/749, 750
See application file for complete search history.

(56) References Cited

U.S. PATENT DOCUMENTS

| | | | | |
|---|---|---|---|---|
| 9,554,484 B2* | 1/2017 | Rogers | .................... | A61B 5/483 |
| 2003/0219648 A1* | 11/2003 | Zucker | .............. | H01M 10/0436 |
| | | | | 429/124 |
| 2015/0202656 A1 | 7/2015 | Takahashi et al. | | |
| 2015/0235731 A1 | 8/2015 | Park et al. | | |
| 2015/0342523 A1 | 12/2015 | Baik et al. | | |
| 2016/0360612 A1* | 12/2016 | Iwase | ..................... | H05K 3/225 |
| 2017/0169914 A1 | 6/2017 | Sekitani et al. | | |
| 2017/0373284 A1* | 12/2017 | Durstock | .............. | H01M 4/485 |
| 2018/0020982 A1* | 1/2018 | Elsherbini | ............ | A61B 5/6833 |
| | | | | 600/301 |
| 2018/0146545 A1 | 5/2018 | Wang et al. | | |
| 2018/0194101 A1* | 7/2018 | Lima | ......................... | C09J 7/38 |

OTHER PUBLICATIONS

Shi, et al., "Electrochemical Impedance Spectroscopic Study of the Electronic and Ionic Transport Properties of NiF2/C Composites", International Journal of Electrochemical Science, 2011. 6(8): p. 3399-3415.
Shin et al., "Deposition of ZnO on *Bismuth* Species Towards Rechargeable Zn-Based Aqueous Battery", Physical Chemistry Chemical Physics, 2016, 18, 26376.
Shin et al., "Polythiophene Nanofibril Bundles Surface-Embedded in Elastomer: A Route to a Highly Stretchable Active Channel Layer", Advanced Materials, 2015, 27, pp. 1255-1261.
Son et al., "Multifunctional wearable devices for diagnosis and therapy of movement disorders", Nat Nano, 2014. 9(5): p. 397-404.
Song et al., "Kirigami-based stretchable lithium-ion batteries", Scientific Reports,2015, 9 pages.
Song et al., "Photo-oxidative enhancement of polymeric molecular sieve membranes", Nat Commun 2013, 4.
Sousa et al., "Advances and Future Challenges in Printed Batteries", ChemSusChem, 2015, 8, pp. 3539-3555.
Stoyanov, H., et al., "Soft Conductive Elastomer Materials for Stretchable Electronics and Voltage Controlled Artificial Muscles", Advanced Materials, 2013. 25(4): p. 578-583.
Su et al., "In-Plane Deformation Mechanics for Highly Stretchable Electronics", Adv. Mater., 2017, 29, p. 1604989.
Trung et al., "Recent Progress on Stretchable Electronic Devices with Intrisically Stretchable Components", Advanced Materials, 2017.
Wang et al., "A highly stretchable, transparent, and conductive polymer", Science Advances, 2017, vol. 3, No. 3.
Wu et al., "Wearable Electricity Generators Fabricated Utilizing Transparent Electronic Textiles Based on Polyester/Ag Nanowires/ Graphene Core-Shell Nanocomposites", ACS Nano, 2016. 10(7): p. 6449-6457.
Xu et al., "Materials and Fractal Designs for 3D Multifunctional Integumentary Membranes with Capabilities in Cardiac Electrotherapy", Advanced Materials, 2015.27(10): p. 1731-1737.
Xu et al., "Stretchable batteries with self-similar serpentine interconnects and integrated wireless recharging systems", Nat Commun, 2013. 4: p. 1543.
Yan, C., et al., "Stretchable SilverZinc Batteries Based on Embedded Nanowire Elastic Conductors", Advanced Energy Materials, 2014. 4(5): p. 1301396.
Yang et al., ""Cut-and-Paste" Manufacture of Multiparametric Epidermal Sensor Systems", Advanced Materials, 2015, 27, pp. 6423-6430.
Yokota et al. "Ultraflexible organic photonic skin", Sci. Adv., 2016, 2, pp. 1-9.
Zamarayeva et al., "Fabrication of a High-Performance Flexible Silver-Zinc Wire Battery", Advanced Electronic Materials, 2016, p. 1500296.
Zang, J. et al. "Stretchable and High-Performance Supercapacitors with Crumpled Graphene Papers", Scit. Rep. 4, 6492.
Zhang et al., "Mechanic of ultra-stretchable self-similar serpentine interconnects", Acta Materialia 61, 2013, pp. 7816-7827.
Zhang et al, "A hierarchical computational model for stretchable interconnects with fractal-inspired designs", Journal of the Mechanics and Physics of Solids, 72, 2014, pp. 115-130.
Zhuang, Q.C., et al., "Diagnosis of Electrochemical Impedance Spectroscopy in Lithium Ion Batteries", Progress in Chemistry, 2010. 22(6): p. 1044-1057.
International Search Report and Written Opinion for PCT Application No. PCT/US2017/062860, dated Mar. 27, 2018, 16 pages.
Amjadi et al., "Stretchable, Skin-Mountable, and Wearable Strain Sensors and Their Potential Applications: A Review", Advanced Functional Materials, 2016. 26(11): p. 1678-1698.
Bandodkar et al., "Tattoo-based potentiometric ion-selective sensors for epidermal pH monitoring", Analyst, 2013, 138, pp. 123-128.
Bandodkar et al., "Highly Stretchable Fully-Printed CNT-Based ElectrochemicalSensors and Biofuel Cells: Combining Intrinsic and Design-Induced Stretchability", NanoLetters, 2016. 16(1): p. 721-727.
Bandodkar et al., "Wearable Chemical Sensors: Present Challenges and Future Prospects", ACS Sensors, 2016. 1 (5): p. 464-482.
Bandodkar et al., "Tattoo-Based Noninvasive Glucose Monitoring: A Proof-of-Concept Study", Anal. Chem, 2015, 87, pp. 394-398.
Bandodkar et al., "All-Printed Stretchable Electrochemical Devices", Advanced Materials 2015, 27, 3060.
Berchmans, S., et al., "An epidermal alkaline rechargeable Ag—Zn printable tattoo battery for wearable electronics", Journal of Materials Chemistry A, 2014. 2(38): p. 15788-15795.

(56) References Cited

OTHER PUBLICATIONS

Canovas et al., "Balloon-Embedded Sensors Withstanding Extreme Multiaxial Stretching and Global Bending Mechanical Stress: Towards Environmental and Security Monitoring", Advanced Materials Technologies, 2016. 1(5): p. 160061.
Chen et al., "Multiphase design on autonomic self-healing thermoplastic elastomers", Nature Chemistry, 2012, 4, pp. 467-472.
Choi, S. et al., "Highly Elastic binders integrating polyrotaxanes for silicon microparticles anodes in lithium ion batteries", Science, 2017, vol. 357, pp. 279-283.
Choi et al., "Recent developments and directions in printed nanomaterials", Nanoscale, 2015, pp. 3338-3355.
Chun et al., "Free-standing nanocomposites with high conductivity and extensibility", Nanotechnology, 2013, 24, p. 165401.
Dickey, "Stretchable Bioelectronics for Medical Devices and Systems", (Eds: A. J. Rogers, R. Ghaffari, D.-H. Kim), Springer International Publishing, Cham 2016, 3.
Fan, et al., "Fractal design concepts for stretchable electronics", Nat Commun, 2014, 8 pages.
Gaikwad et al., "Highly Stretchable Alkaline Batteries Based on an Embedded Conductive Fabric", Advanced Materials, 2012, p. 50715076.
Gaikwad et al., "Highly Flexible, Printed Alkaline Batteries Based on Mesh-Embedded Electrodes", Advanced Materials 2011, 23, 3251.
Hong, S., et al., "3D Printing of Highly Stretchable and Tough Hydrogels into Complex",Cellularized Structures. Advanced Materials, 2015. 27(27): p. 4035-4040.
Hu et al., "Direct Pen Writing of Adhesive Particle-Free Ultrahigh Silver Salt-Loaded Composite Ink for Stretchable Circuits", ACS Nano, 2016, 10(1), pp. 396-404.
Huang et al., "Materials and Designs for Wireless Epidermal Sensors of Hydration and Strain", Advanced Functional Materials, 2014. 24(25): p. 3846-3854.
Imani et al., "A wearable chemical-electrophysiological hybrid biosensing system for real-time health and fitness monitoring", Nat Commun, 2016, pp. 1-7.
Jeerapan et al., "Stretchable biofuel cells as wearable textile-based self-powered sensors", J. Mater. Chem, 2016, 4, pp. 18342-18353.
Jung et al., "Wearable Fall Detector using Integrated Sensors and Energy Devices", Scientific Reports, 2015, 9 pages.
Kamyshny et al., "Conductive Nanomaterials for Printed Electronics", Small, 2014, pp. 3515-3535.
Kassal et al., "Smart bandage with wireless connectivity for uric acid biosensing as an indicator of wound status", Electrochemistry Communications, 2015. 56: p. 6-10.
Kettlgruber, G., et al., "Intrinsically stretchable and rechargeable batteries for self powered stretchable electronics", Journal of Materials Chemistry A, 2013. 1(18): p. 5505-5508.
Kim, D-H., "Stretchable Electronics: Materials Strategies and Devices", Advanced Materials, 2008, 20, pp. 4887-4892.
Kim et al., "Noninvasive Alcohol Monitoring Using a Wearable Tattoo-Based Iontophoretic-Biosensing System", ACS Sensors, 2016, 1, pp. 1011-1019.
Kim et al., "Encapsulated, High-Performance, Stretchable Array of Stacked Planar Micro-Supercapacitors as Waterproof Wearable Energy Storage Devices", ACS Applied Materials & Interfaces, 2016. 8(25): p. 16016-16025.
Kim et al., "Advanced Materials for Printed Wearable Electrochemical Devices: A Review", Advanced Electronic Materials, 2016, 15 pages.
Kumar et al., "All-Printed, Stretchable Zn—Ag2O Rechargable Battery via, Hyperelastic Binder for Self-Powering Wearable Electronics", Adv. Energy Mater., 2017, p. 1602096.
Kwon et al., "Cable-Type Flexible Lithium Ion Battery Based on Hollow Multi-Helix Electrodes", Advanced Materials, 2012, 24, pp. 5192-5197.
Kwon et al., "On-Demand Separation of Oil-Warer Mixtures", Advanced Materials 2012, 24, 5192.
Lee et al., "A graphene-based electrochemical device with thermoresponsive microneedles for diabetes monitoring and therapy", Nat Nano, 2016, 11, p. 566-572.
Lee et al., "Stretchable GaAs Photovoltaics with Designs That Enable High Areal Coverage", Adv. Mater., 2011, 23, pp. 986-991.
Li et al., "Toward a Stretchable, Elastic, and Electrically Conductive Nanocompostite: Morphology and Properties of Poly[styrene-b-(ethylene-co-butylene)-b-styrene]/Multiwalled Carbon Nanotube Composites Fabricated by High-Shear Processing", Macromolecules, 2009, 42, pp. 2587-2593.
Li et al., "An analytical mechanics model for the island-bridge structure of stretchable electronics", Soft Matter, 2013, pp. 8476-8482.
Liang et al., "Elastomeric polymer light-emitting devices and displays", Nat Photon, 2013.7(10): p. 817-824.
Lipomi, D., "Stretchable Figures of Merit in Deformable Electronics", Advanced Materials, 2016, 28, pp. 4180-4183.
Lipomi et al., "Stretchable Organic Solar Cells", Adv. Mater., 2011, 23, pp. 1771-1775.
Liu, D., et al., "An Effective Mixing for Lithium Ion Battery Slurries", Advances in Chemical Engineering and Science, 2014. vol. 04 No. 04: p. 14.
Lu, N. et al., "Flexible and Stretchable Electronics Paving the Way for Soft Robotics", Soft Robotics, vol. 1, No. 1, 2014, pp. 53-62.
Matsuhisa et al., Printable elastic conductors with a high conductivity for electronic textile applications. Nat Commun, 2015. 6.
Matsuhisa et al., "Printable elastic conductors by in situ formation of silver nanoparticles from silver flakes", Nature Materials, 16, 2017, pp. 834-840.
Meng et al., "All-Graphene Core-Sheath Microfibers for All-Solid-State, Stretchable Fibriform Supercapacitors and Wearable Electronic Textiles", Advanced Materials, 2013.25(16): p. 2326-2331.
Mishra, R.K. et al., "Wearable Flexible and Stretchable Glove Biosensor for On-Site Detection of Organophosphorous Chemical Threats", ACS Sensors, 2017, vol. 2, pp. 553-561.
Mohan et al., "Merging of Thin-and Thick-Film Fabrication Technologies: Toward Soft Stretchable "Island-Bridge" Devices", Adv. Mater. Technol., 2017, 2, pp. 1600284.
Nyein et al., "A Wearable Electrochemical Platform for Noninvasive Simultaneous Monitoring of Ca2+ and pH", ACS Nano, 2016, 10, pp. 7216-7224.
Pan, et al., "Two-dimensional digital image correlation for in-plane displacement and strain measurement: a review", Measurement Science and Technology, 2009. 20(6): p. 062001.
Park et al., "Design of conductive composite elastomers for stretchable electronics", Nano Today 2014, 9, pp. 244-260.
Park et al., "Soft, stretchable, fully implantable miniaturized optoelectronic systems for wireless optogenetics", Nat Biotech, 2015. 33(12): p. 1280-1286.

\* cited by examiner

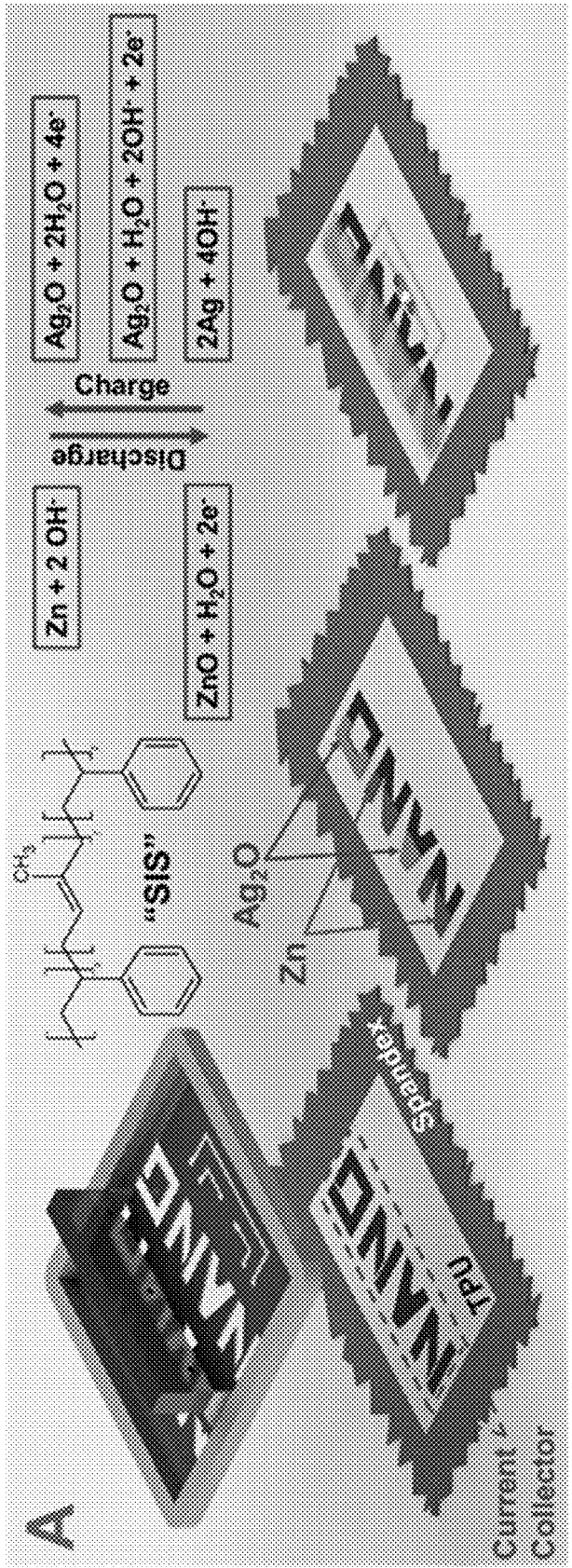
FIG. 1D
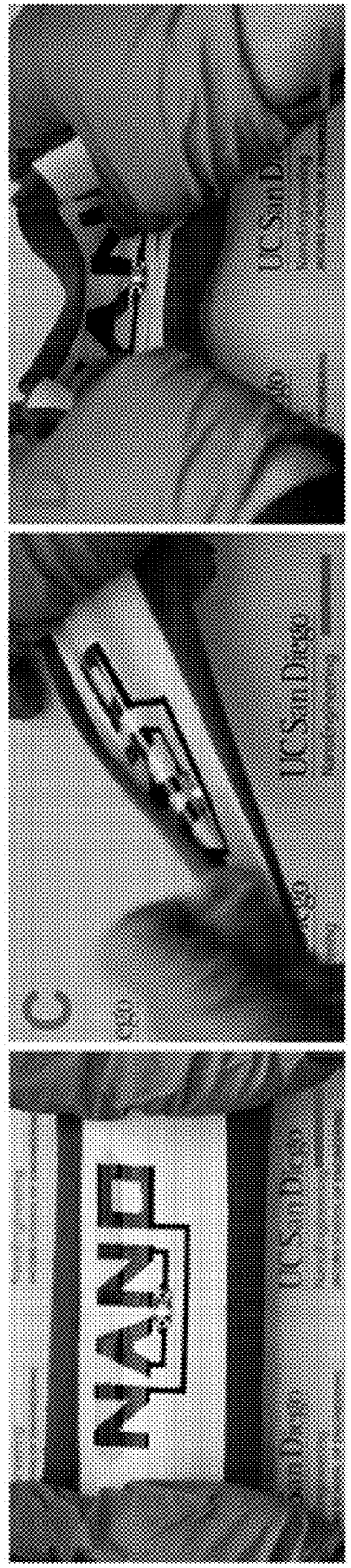
FIG. 1E
FIG. 1F
FIG. 1G

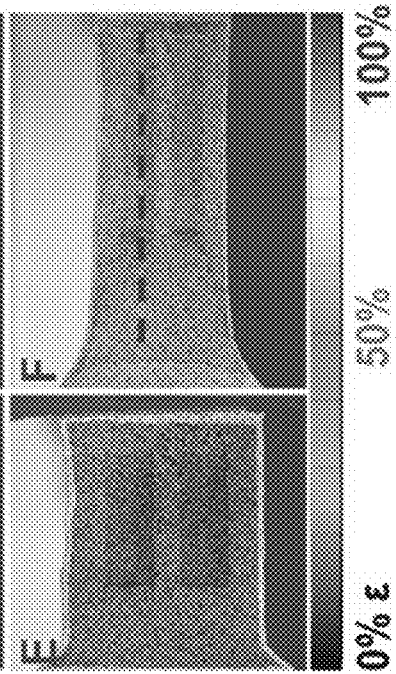
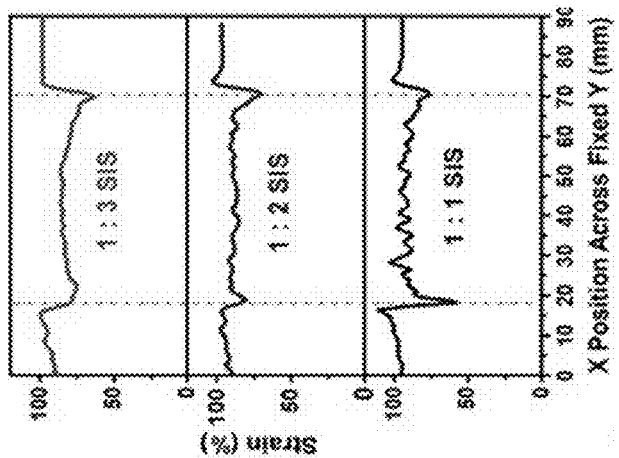
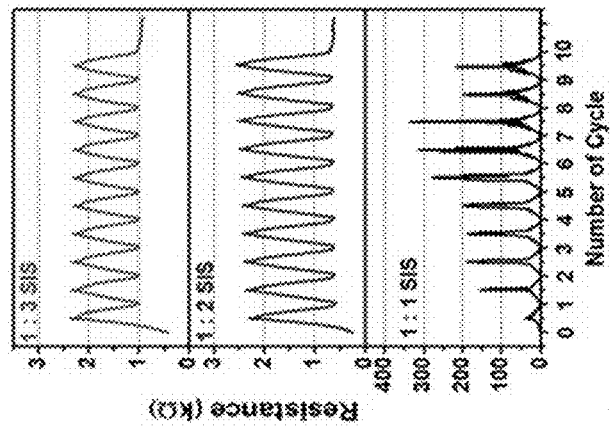
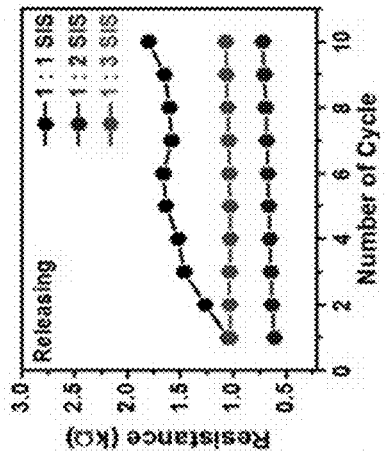
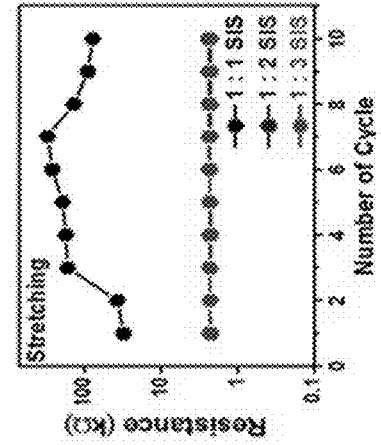
FIG. 2A
FIG. 2B
FIG. 2C
FIG. 2D
FIG. 2E

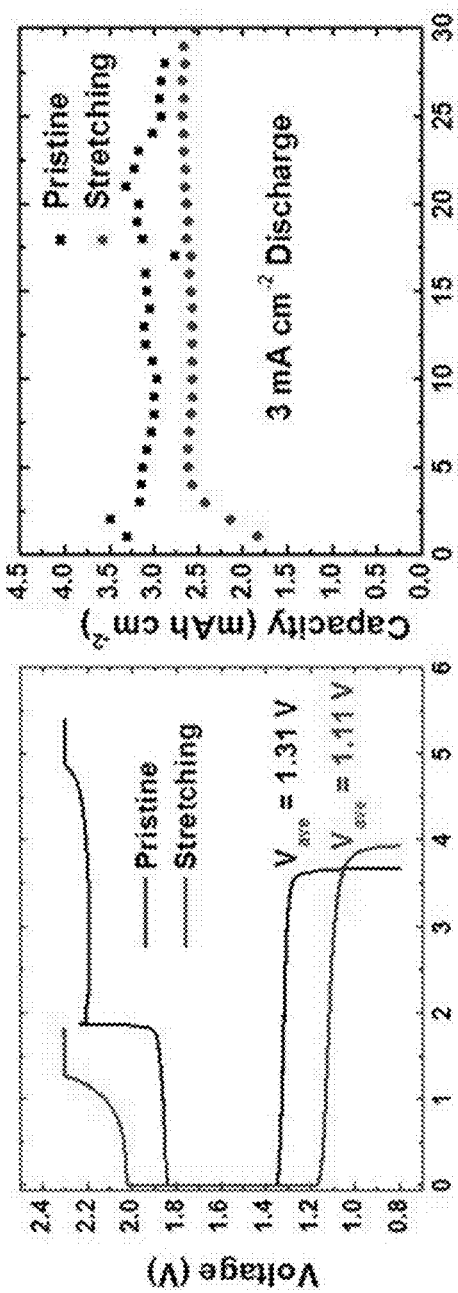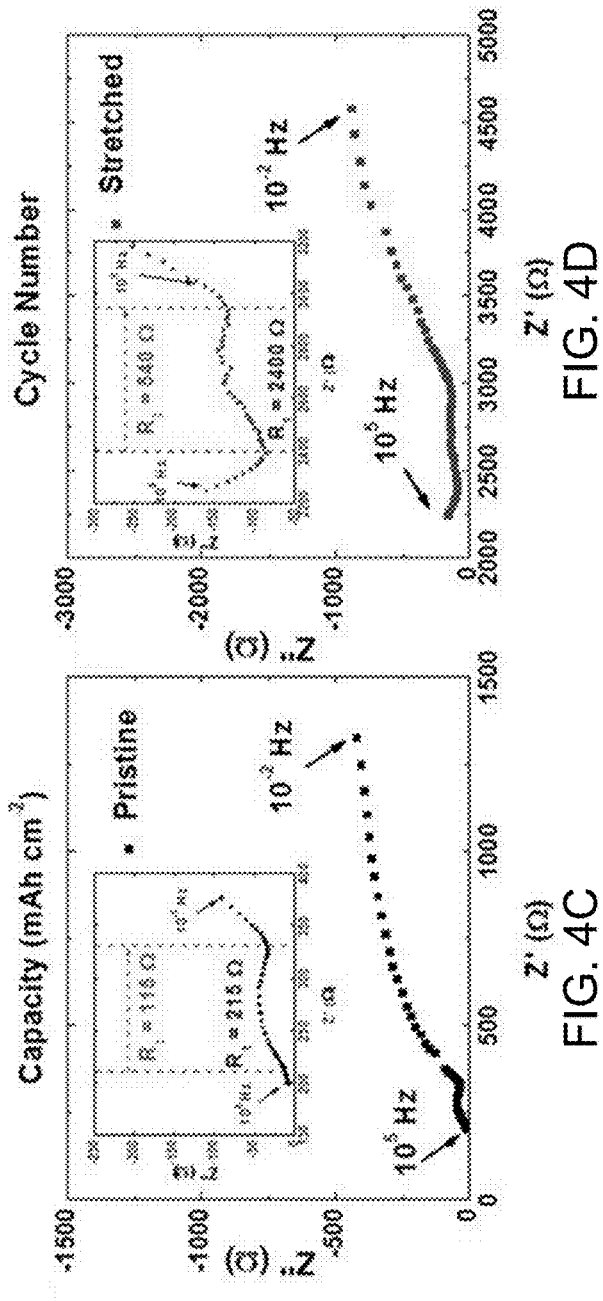
FIG. 4A  FIG. 4B  FIG. 4C  FIG. 4D

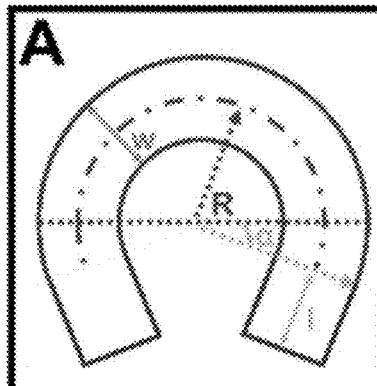
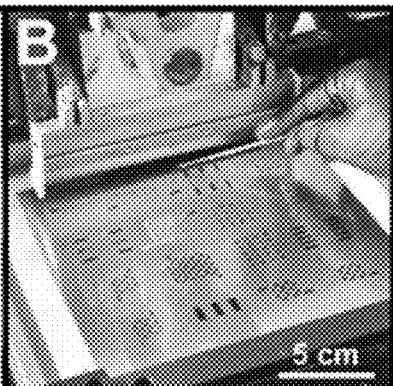
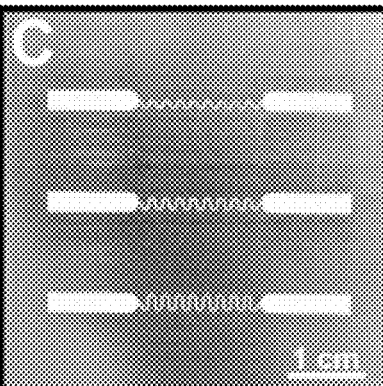
FIG.12A  FIG.12B  FIG.12C
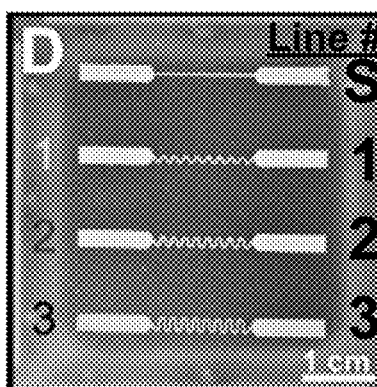
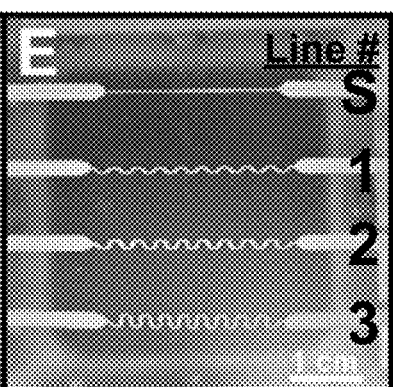
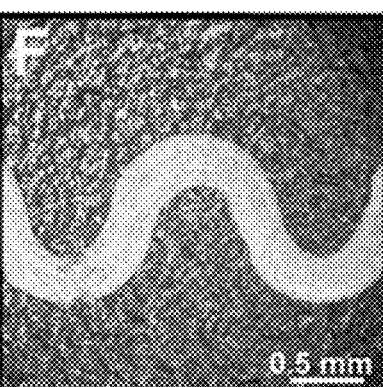
FIG.12D  FIG.12E  FIG.12F
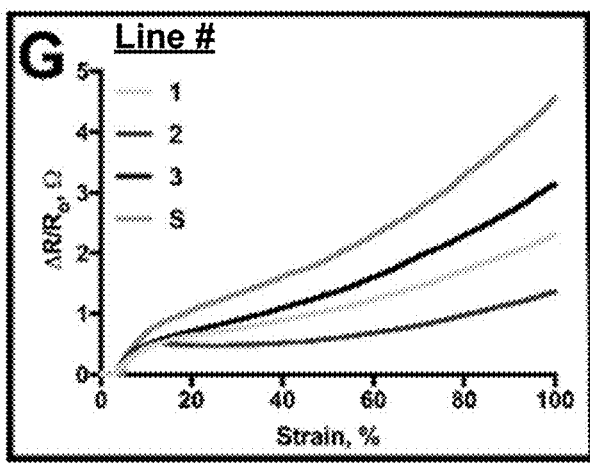
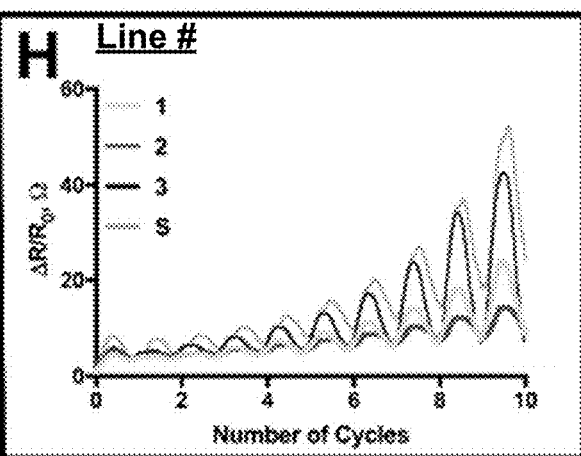
FIG.12G  FIG.12H

HYPERELASTIC BINDER FOR PRINTED, STRETCHABLE ELECTRONICS

CROSS-REFERENCE TO RELATED APPLICATIONS

This patent is a continuation of U.S. patent application Ser. No. 15/820,284 entitled "HYPERELASTIC BINDER FOR PRINTED, STRETCHABLE ELECTRONICS" filed on Nov. 21, 2017, now U.S. Pat. No. 10,143,081, which claims the priority to and benefits of U.S. Provisional Patent Application No. 62/425,036 entitled "HYPERELASTIC BINDER FOR PRINTED, STRETCHABLE ELECTRONICS" filed on Nov. 21, 2016. The entire contents of the aforementioned patent applications are incorporated by reference as part of the disclosure of this patent document.

STATEMENT REGARDING FEDERALLY SPONSORED RESEARCH OR DEVELOPMENT

This invention was made with government support under grant No. ECCS-1542148 awarded by the National Science Foundation (NSF) and grant No. DE-AR0000535 awarded by Advanced Research Projects Agency-Energy (ARPA-E). The government has certain rights in the invention.

TECHNICAL FIELD

This patent document relates to systems, devices, and processes for flexible and stretchable electronics.

BACKGROUND

Conformal electronics are a new, emerging class of electronic devices that can conform to complex non-planar and deformable surfaces, such as living tissue like skin, textiles, robotics and others. Conformal electronic devices can include electric circuits and devices formed on flexible substrates that can be applied to and conform to a variety of surface geometries. For example, some flexible electronics have a capability that they can wrap or be bended, and can be shaped to fit to curvilinear surfaces.

SUMMARY

Disclosed are compositions, devices, systems and fabrication methods for stretchable composite materials including triblock copolymer materials (e.g., thermoplastic elastomers) synthesized with a utility material to produce elastic, functional materials, which can be used to form stretchable electronic components and devices.

In some aspects, a stretchable electronics device includes a stretchable substrate including an elastic and electrically insulative material structured to conform to an outer surface of an object; and an electrode arranged over the stretchable substrate, in which the electrode is formed from an elastic composite material including an electrical conductor, and a multi-block copolymer configured to form a hyperelastic binder that creates contacts between particles of the electrical conductor within a network formed by the multi-block copolymer.

In some aspects, a stretchable battery includes a stretchable substrate including an elastic and electrically insulative material structured to conform to an outer surface of an object; a current conductor layer attached to the stretchable substrate, in which the current conductor layer includes a first elastic composite material including a first electrical conductor and a multi-block copolymer configured to form a first hyperelastic binder that creates contacts between particles of the first electrical conductor within a network formed by the multi-block copolymer; an anode attached to the current conductor layer and arranged over the stretchable substrate, in which the anode includes a second elastic composite material including a second electrical conductor and the multi-block copolymer configured to form a second hyperelastic binder that creates contacts between particles of the second electrical conductor within a network formed by the multi-block copolymer; and a cathode arranged over the stretchable substrate, in which the cathode includes a third elastic composite material including a third electrical conductor and the multi-block copolymer configured to form a third hyperelastic binder that creates contacts between particles of the third electrical conductor within a network formed by the multi-block copolymer, in which the stretchable battery is operable to store energy while undergoing stretching.

In some aspects, a stretchable battery including a stretchable substrate including an elastic and electrically insulative material structured to conform to an outer surface of an object; a first electrical interconnection structure and a second electrical interconnection structure each attached to the stretchable substrate and having a periodic curved horseshoe geometry configured to connect unit cell regions positioned on the electrical interconnection structure, in which the first and the second interconnection structures include a first elastic composite material including a first electrical conductor and a multi-block copolymer configured to form a first hyperelastic binder that creates contacts between particles of the first electrical conductor within a network formed by the multi-block copolymer; a plurality of current conductor components attached to the electrical interconnection structure at the unit cell regions, in which the current conductor layer includes a second elastic composite material including a second electrical conductor and a multi-block copolymer configured to form a second hyperelastic binder that creates contacts between particles of the second electrical conductor within a network formed by the multi-block copolymer; a plurality of anodes attached to the current conductor component over the unit cell regions of the first electrical interconnection structure, in which the anodes include a third elastic composite material including a third electrical conductor and the multi-block copolymer configured to form a third hyperelastic binder that creates contacts between particles of the third electrical conductor within a network formed by the multi-block copolymer; and a plurality of cathodes attached to the current conductor component over the unit cell regions of the second electrical interconnection structure, in which the cathodes include a fourth elastic composite material including a fourth electrical conductor and the multi-block copolymer configured to form a fourth hyperelastic binder that creates contacts between particles of the fourth electrical conductor within a network formed by the multi-block copolymer.

In some aspects, a method for producing a stretchable electronics device includes providing an electrically conductive ink that includes an elastic composite material including an electrically conductive material and a multi-block copolymer configured to form a hyperelastic binder that creates contact between the electrically conductive material and the multi-block copolymer; producing a first structure on a stretchable substrate by printing the electrically conductive ink through a first portion of a stencil structured to have a first design to form the geometry of the first structure, in which the stretchable substrate includes an elastic material structured to conform to an outer surface of an object; and producing a second structure on the stretchable substrate to produce a stretchable electronics article by printing the electrically conductive ink through the first portion of the stencil, or a second portion of the stencil structured to have a second design, or both the first portion and the second portion, to form the geometry of the second structure, in which the stretchable electronics article is able to stretch at least 500% in at least one direction and to exhibit electrical conductivity in the first structure while being stretched.

In some aspects, an elastic composite material includes a first material having a particular electrical, mechanical or optical property; and a multi-block copolymer configured to form a hyperelastic binder that creates contact between the first material and the multi-block copolymer, in which the elastic composite material is structured to stretch at least 500% in at least one direction of the material and to exhibit the particular electrical, mechanical or optical property imparted from the first material.

Implementations of the disclosed technology can include one or more of the following features. In some example embodiments, the disclosed stretchable composite materials include an elastic, conductive ink having hyperelastic properties based on the formulation of triblock copolymers, used as a hyperelastic binder, with conductive utility material(s), in which the hyperelastic binder is capable of tolerating high loadings of inelastic materials without sacrificing the elastic properties of the stretchable composite.

In some example embodiments, a stretchable zinc-silver (I) oxide rechargeable battery in accordance with the present technology includes polystyrene-polyisoprene-polystyrene as a binder for elastic, electroactive inks. The example multi-component device can be produced by the synthesis of multiple elastic inks including composite metal/metal oxide powders (e.g., carbon black, zinc, silver (I) oxide) for its respective functionality. The example stretchable rechargeable battery can be used to self-power stretchable electronics through various deformations such as 100% stretching, twisting, and indentations.

In some example embodiments, formulations of conductive inks for stretchable electronics, implementation of random composite inks and deterministic patterning using inexpensive, high-throughput screen printing of stretchable electronics for epidermal, textile, robotics, internet of things (JOT), and in-mold applications, among others. In such embodiments, the stretchable electronics include a hyperelastic structure of "nanoislands" and/or "nanobridges" formed from highly conductive, elastic inks including example triblock copolymers and utility materials. The example island-bridge designs provide a macro level of stretchability for such engineered components and devices, e.g., produced via printing the conductive, elastic inks.

These, and other, embodiments and techniques are described throughout this document.

BRIEF DESCRIPTION OF THE DRAWINGS

FIG. 1D shows a diagram of an example embodiment of a stretchable electronics $Zn$—$Ag_2O$ battery in accordance with the present technology produced using an example elastic, conductive composite ink on a stretchable textile.

FIGS. 1E-1I show photographs of the example stretchable battery shown in FIG. 1D while undergoing various stretching, twisting and straining.

FIGS. 2A-2E show images and data plots of strain mapping evaluations of example rectangular carbon electrodes formed using the example composite ink.

FIGS. 4A-4D shows data plots depicting the electrochemical performance of the example stretchable battery.

FIGS. 12A-12H show a diagram depicting the geometry of example serpentine bridges and images and data plots pertaining to evaluation of uniaxial stretching of example embodiments of stretchable IB electronics devices.

DETAILED DESCRIPTION

Figure 1A:
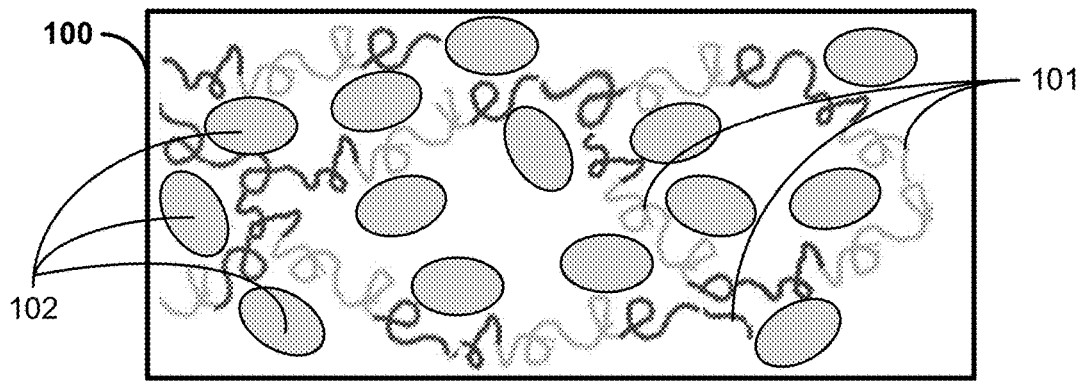
FIG. 1A shows an illustration of an example elastic composite material 100 in accordance with the present technology.

Conformal electronics are a new, emerging class of electronic devices that can conform to complex non-planar and deformable surfaces, such as living tissue like skin, textiles, robotics and others. Composites used for conformal electronics can be amenable to high-throughput, low-cost, additive printing technologies that include screen, inkjet, flexography, and 3D printing. However, the properties of the functional and elastic materials are mutually antagonistic to the other, thus achieving start-of-the-art functional (bulk) properties and high elasticity has been limited.

The advent of flexible/stretchable electronics has cultivated the next generation of sensors, photovoltaics, paper-like displays, wearable/implantable electronics e-textiles, optics, and soft robotics. Unlike their brittle and rigid predecessors, soft flexible/stretchable electronics have the potential to intimately integrate with curvilinear surfaces while withstanding the complex deformations common of human organs, textiles, or robotics. Unfortunately, the progress of stretchable systems, specific to their mobility and independence, is currently constrained by bulky and rigid powering sources. Batteries hold the most promise owing to their high power and energy densities, rechargeability, and low-cost.

Some examples of existing stretchable batteries have been fabricated through different approaches, such as deterministic composite and random composite architectural approaches. The deterministic approach relies on subtractive methods to render otherwise rigid materials, with bulk properties, into deterministic structures such as "island-bridge" or "cable-type" batteries. By engineering elasticity with high-performance rigid electrodes, these stretchable batteries can withstand some levels of strain, but without intrinsically stretching them. As such, stretchable batteries produced via the deterministic approach are not truly stretchable devices. The random composite approach embeds percolations of highly conductive fillers (e.g., >$10^7$ S $m^{-1}$, silver nanowires and carbon nanomaterials) into an elastomeric matrix. Unlike deterministic composite, these devices are intrinsically stretchable as fillers maintain electrical contact by sliding along each other during stretching. However, while some of these intrinsically stretchable batteries have been reported, none of the stretchable devices produced via the random composite approach are completely elastic systems. For example, the cycle ability, current density, or areal capacity of these random composite produced batteries are compromised when a rigid component undergoes large physical strain. Moreover, both deterministic and random composite-designed batteries are not economical because they rely on extremely expensive and low-throughput fabrication methods, such as lithographic, spray/dip coating, or "cut-and-paste" techniques.

Currently, printed, non-rechargeable batteries is an emerging market supporting many wearable and disposable electronics, e.g., with one study expecting the market value to reach $1.2 billion by 2017, CAGR 46% from 2012. Presently, individual components are fabricated using a single, inexpensive printing step through either dispensing, screen, roll-to-roll, or inkjet printing of composite inks.

Unlike comparable coating technologies, such as spray or dip coating, screen printing can actively control the design that can potentially combine both deterministic and random composites. The higher viscosity requirements of screen printing allows high loadings of conductive fillers towards superior elastic performance and higher battery operation. The rheology of the ink is controlled by the composite formulation of electroactive fillers, a binder, and a specific solvent. The binder plays the role of holding the ink components together and in dictating the flexible and stretchable nature of the inks. The synthesis of stretchable inks is highly challenging since the battery experiences significantly higher strain levels during stretching as compared to just bending. The printing technologies and random composite-based inks can be used to fabricate cost-effective and intrinsically stretchable batteries. The fundamental challenge of using random composite is that the electrochemical properties of the fillers and elastic matrix are mutually detrimental to the other. This approach becomes overwhelmingly challenging for printed, stretchable batteries with poorly conductive, electroactive fillers (e.g., ~$10^5$ S $m^{-1}$).

New innovations in highly elastic matrix would greatly benefit the advancement of stretchable power source devices, e.g., in particular, specially formulated inks that are formulated to allow the printed batteries to be stretched 100% multiple times.

Disclosed are compositions, devices, systems and fabrication methods for stretchable composite materials including triblock copolymer materials (e.g., thermoplastic elastomers) synthesized with a utility material to produce elastic, functional materials, which can be used to form stretchable electronic components and devices. Example embodiments of the disclosed stretchable composite materials include an elastic, conductive ink having hyperelastic properties based on the formulation of triblock copolymers, used as a hyperelastic binder, with conductive utility material(s), in which the hyperelastic binder is capable of tolerating high loadings of inelastic materials without sacrificing the elastic properties of the stretchable composite.

Various functionalities for the disclosed elastic, functional composites, e.g., such as inks, can range from conductors, insulators, dielectrics, semiconductors and ceramics using both inorganic and/or organic functional fillers. In some embodiments in accordance with the disclosed technology, the use of these triblock copolymers with specific percolate, functional fillers can yield fabrication of printed stretchable electronics devices and systems for various technologies, for example, including but not limited to conductive components, electrical circuits, photovoltaic devices, thermoelectric devices, piezoelectric devices, light-emitting devices, electrochemical sensors, supercapacitors, physical sensors, triboelectrics, actuators, batteries, and biofuel cells. Such printed stretchable technologies can be mounted to a textile or skin for stretchable applications that require comfortability and high performance under deformation, as well as be used for in-mold electronics.

In some example embodiments, a stretchable zinc-silver (I) oxide rechargeable battery in accordance with the present technology includes polystyrene-polyisoprene-polystyrene as a binder for elastic, electroactive inks. The example multi-component device can be produced by the synthesis of multiple elastic inks with composite metal/metal oxide powders (e.g., carbon black, zinc, silver (I) oxide) for its respective functionality. The example stretchable rechargeable battery can be used to self-power stretchable electronics through various deformations such as 100% stretching, twisting, and indentations.

In some example embodiments, formulations of conductive inks for stretchable electronics, implementation of random composite inks and deterministic patterning using inexpensive, high-throughput screen printing of stretchable electronics for epidermal or textile applications. In such embodiments, the stretchable electronics include a hyperelastic structure of "nanoislands" and/or "nanobridges" formed from highly conductive, elastic inks including example triblock copolymers and utility materials. The example island-bridge designs provide a macro level of stretchability for such engineered components and devices, e.g., produced via printing the conductive, elastic inks.

In some implementations, example embodiments of highly elastic, conductive inks are used in low-cost screen printing techniques to manufacture example embodiments of an all-printed stretchable Zn—$Ag_2O$ rechargeable battery in accordance with the present technology. The example inks possess attractive hyperelastic properties (e.g., ~1300% elongation) of polystyrene-block-polyisoprene-block-polystyrene (SIS) to provide an elastic binder for customizable, printable inks, which can be employed to produce stretchable batteries. For example, due to unique block polymeric structure of long polyisoprene chain and short polystyrene terminal ends, SIS has superior elasticity and simpler processing compared to common elastomers, such as Exoflex® that requires an additional curing (vulcanization) step to form the 3D crosslinked network to impart truly elastic behavior. In contrast, for example, SIS can be incorporated in higher loadings while maintaining the mechanical and electrochemical properties of the battery, as demonstrated in example implementations of the highly elastic, conductive inks described herein. The example resulting rechargeable Zn—Ag$_2$O battery demonstrates a reversible capacity density (e.g., ~2.5 mAh cm$^{-2}$) even after multiple iterations of 100% stretching, and represents an intrinsically stretchable battery with the highest reversible capacity and discharge current density, manufacturable by inexpensive printing methods described herein. The example SIS-based printed battery can withstand other severe torsional strains relevant to the wearer's movement. In example implementations, the mechanical properties of the stretchable battery were evaluated using digital image correlation (DIC) and scanning electron microscopy (SEM), and the attractive electrochemical cycling, impedance and mechanical properties of the stretchable battery are presented.

Example Embodiments

In accordance with some embodiments of the present technology, an elastic composite material for stretchable electronics includes (i) a copolymer material, such as a block copolymer, and (ii) a utility material, such as an electrical conductor, insulator, or semiconductor material. In some embodiments, the elastic composite material includes one or more utility materials. In some embodiments, the elastic composite material further includes one or more additives.

In some embodiments, the copolymer material includes a triblock copolymer (ABA), e.g., such as polystyrene-block-polyisoprene-block-polystyrene (SIS), styrene-ethylene/butylene-sytrene (SEBS), styrene-ethylene/propylene-styrene (SEPS), and other triblock copolymers with grafted chains on the midblock polymer. In such embodiments, the triblock copolymer forms a phase separation of soft isoprene blocks that are physically crosslinked by nanoclusters glassy styrene blocks. The mechanical behavior of SIS's highly elastic network is similar to network structure of chemically crosslinked rubber through irreversible vulcanization with the added benefit of being processable as a conductive ink. As such, the triblock copolymers include hyperelastic properties that can tolerate higher loadings of inelastic, functional materials to form new materials, like inks, without sacrificing elastic properties of the formulated ink. For example, SIS was used to formulate an example ink with silver flake, and the resulting elastic conductor demonstrated an extremely high conductivity of 2281 S/cm at 0% and fractured at 400%. The higher loading of functional or utility material(s) with the example soft, hyperelastic triblock copolymer materials can achieve devices with bulk-like structure and performance while being mechanically durable.

FIG. 1A shows an illustration of an example elastic composite material 100 in accordance with the present technology. The elastic composite material 100 includes a copolymer 101 and one or more utility materials 102 dispersed in the material 100. In some example embodiments of the elastic composite material 100, the copolymer 101 includes a triblock copolymer, such as SIS. Also, in some example embodiments, the copolymer 101 includes other examples of a thermoplastic elastomer including styrene-ethylene/butylene-styrene (SEBS) block copolymer, styrene-ethylene/propylene-styrene (SEPS), styrene-butadiene-styrene (SBS) block copolymer, or other triblock copolymer with grafted chains on the midblock polymer. In some examples, the copolymer 101 includes fluorine rubber. The utility material 102 and the copolymer material 101 form a highly conductive network based on the contacts of the utility material 102 with the copolymer 101. In the example of SIS, SEBS or SEPS as the copolymer 101, the example copolymer provides superior elastic properties to the elastic composite material 100 which allows one to reduce the amount of non-conductive polymer material and load more conductive fillers that results in more functional utility of the elastic composite 100, in which the network still maintains a stable performance. In some example embodiments, the elastic composite material 100 includes two or more types of elastic copolymer materials 101 in the composite material.

In some example embodiments of the elastic composite material 100, the utility material 102 includes one or more types of materials, which are selected based on their electrical, optical and/or mechanical properties to provide a functionality to the elastic composite material 100. In some examples, the utility material 102 includes a bulk or micro-/nano-scale material based on functional properties, such as an electrical conductor, insulator, oxide ceramic, non-oxide ceramics, electrochemical, triboelectric, actuators, or semiconductor, optical or opto-electrical material, MEMS materials, etc.

In some example embodiments, the elastic composite material 100 includes one or more additive materials. The additive materials can include other metals, polymers, ceramics, composite materials, and/or micro-/nano-materials, e.g., nanoparticles, nanowires, nanofibers, nanoflakes, graphene or carbon nanotubes (CNTs), or other material. For example, a 1-2% additive material can provide high aspect ratio fillers that improve durability, printability, conductivity, and appearance (e.g., color or degree of transparency/opaqueness) of the elastic composite material 100. In some examples, the additive material can include mineral oil to improve the durability (e.g., 1-2%). In some examples, the additive material can include ZnO and bismuth oxide to improve battery performance for a stretchable electronic device, such as stabile, recharge cycling (e.g., 5-10% each). In some examples, the additive material can include polyamide brushes can improve the durability by imparting self-healing properties. In some examples, the additive includes a solvent that can be used to improve the formulation of elastic composite material 100 as an ink. Such example solvents can be included such that the Hansen solubility parameter is matched with the copolymer constituent, e.g., copolymer material 101, such as in a range of 7.7 to 9.4.

For example, the additive material can include polyvinylidene fluoride (PVDF), e.g., which can provide added durability to the elastic composite material 100 without affecting the functional properties provided by the utility material 102, such as electrical conductivity. For example, a 1:1 ratio of SIS and PVDF in a solvent mix of Toluene/NMP can be used improve the durability of the ink to be printed. In some example implementations, the elastic composite material 100 can include SIS, a conductive material (e.g., Zn powder (80% Zn: 20% Carbon SP)), and additive PVDF (e.g., 5% PVDF in NMP). For example, 1 gram of a SIS-PVDF mixture (e.g., 0.1 g SIS, 0.15 g PVDF in 5 mL Toluene/NMP) is mixed with 1 gram of the Zn powder, in which the mix is repeated and printed on a substrate (e.g., polyimide).

Figure 1B:
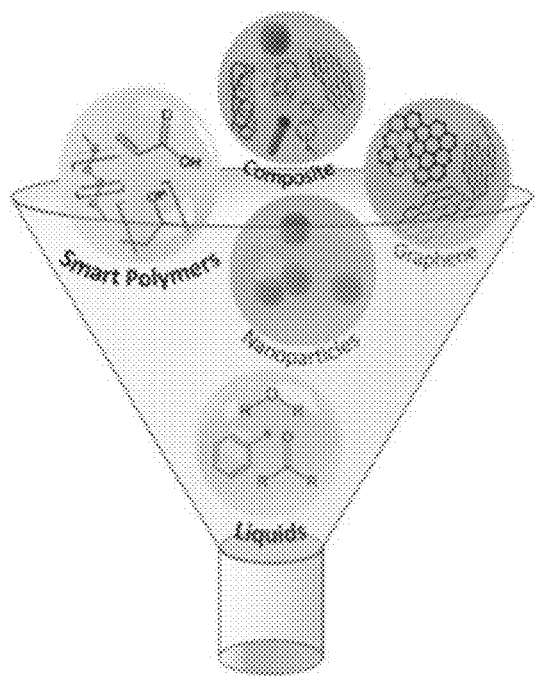
FIG. 1B shows an illustration of example constituents of a solution to produce an elastic composite material.

FIG. 1B shows an illustration of example constituents of a solution to produce an elastic composite material 100. In this example, the example constituents of the solution include the 'smart' polymer, and the utility and additive materials, e.g., nanoparticles, graphene and/or other composite, mixed in a solvent liquid. For example, the solution can be applied to a surface to produce the elastic composite material on a substrate using a variety of techniques, e.g., including spraying, screen-printing, inject printing, doctor blading, spin-coating, and 3D printing on any surface. For example, modification of solvent ratios can allow printing of subsequent layers. For example, the ratio (of the copolymer material 101 (e.g., thermoplastic elastomer) and the utility material 102 can affect the functional performance and durability of the elastic composite material 100. For example, addition of a thermoplastic polymer <3% with addition of another polymer (e.g., additive material) can improve the durability of the product.

Figure 1C:
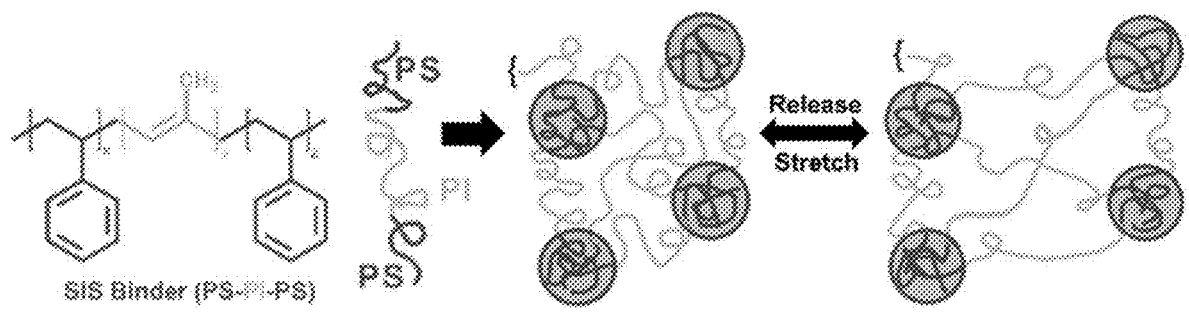
FIG. 1C shows an illustrative diagram depicting the release and stretch states of an example of the copolymer of the elastic composite material.
Figure 1H:

FIG. 1C shows an illustrative diagram depicting the release and stretch states of an example of the copolymer 101, e.g., SIS. As depicted in the diagram, the block-polystyrene portion of polymer chains forms a physical crosslinking e.g., due to the affinity of styrene to each other, and the block-polystyrene crosslinking center is interconnected by long chains of the block-polyisoprene. The copolymer 101 forms a hyperelastic binder that creates contacts between particles of the utility material 102 (and/or any additive materials) within a polymeric network formed by the copolymer 101, contained within the overall elastic composite material 100. As such, the elastic composite material 100 is able to stretch and release independent of other materials to augment polymers of the material. For example, unlike some conventional stretchable materials that use polymers, the elastic composite material 100 does not require a cross-linker for cross-linking strands of a polymer in the elastic composite material.

In some embodiments in accordance with the present technology, stretchable electronics devices include the elastic composite materials to form the components of the device, e.g., including conductive components, insulating components, and/or semiconductor components. In some examples, the elastic composite materials are used to produce a printable stretchable battery in accordance with the present technology. Printed batteries have already been well established by powering radio frequency identification devices (RFIDs), wearable devices, sensors for remote monitoring, and electronic displays. For example, printed batteries have been used to power transdermal drug delivery. These devices are primarily used to deliver arthritic or cosmetic drugs on to curved surfaces of the skin that deform. At the moment, many of these printed batteries are only flexible, but not stretchable, and therefore can diminish the performance and wearer's comfort in a wearable system. The present technology includes a highly stretchable rechargeable battery that can be printed onto stretchable substrates and later applied to no curvilinear substrates such as skin, textiles, and robotics. For example, a printed device such as a battery can be screen-printed on to a film with an adhesive backing, which can be transfer to any surface such as skin, textile, automotive, electronics casing. In some instances, the transfer of textile can use heat to transfer the film onto a shirt. Such devices have great potential to power other wearable electronics without diminishing the conformability and performance of the entire, wearable system.

FIG. 1D shows a diagram of an example stretchable electronics device, i.e., a $Zn$—$Ag_2O$ battery, produced using an example elastic, conductive composite ink on a stretchable textile. In some implementations, the example stretchable $Zn$—$Ag_2O$ battery can be fabricated using screen printing techniques to form the elastic components of the $Zn$—$Ag_2O$ battery on a stretchable textile using the example composite ink having the SIS-hyperelastic binder. The diagram depicts an example redox charge and discharge reaction exhibited by the battery.

For example, the attractive mechanical properties of the elastic, conductive composite ink lead to the intrinsically stretchable, rechargeable and printable $Zn$—$Ag_2O$ battery that can withstand a variety of severe mechanical strains. In the example shown in FIG. 1D, two stretchable batteries were printed in a "NANO" design directly on top of the thermoplastic polyurethane (TPU) head sealed onto a textile (e.g., spandex). On the "NANO" current collector, the respective electrodes were printed to form two batteries, i.e., the "NA" and "NO" designs, which are connected in series to power a load or device, e.g., a 3V wearable-based LED in this example. In this example, an additional seal between "A" and the second "N" was applied, e.g., to avoid possible short circuit.

Figure 1I:
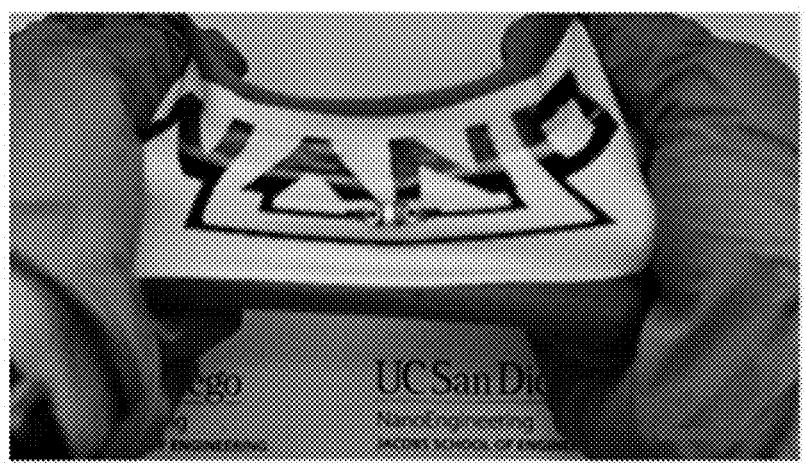

FIGS. 1E-1I show photographs of the example stretchable battery while being 0% stretched (FIG. 1E), while being twisted (FIG. 1F), while undergoing indentation strains (FIG. 1G), while being 100% stretched (FIG. 1H), and while being stretched biaxially (FIG. 1I). The scale bar in the photographs of FIGS. 1E-1I is 2.25 cm.

As shown in the photographs of FIGS. 1E-1I, the example stretchable "NANO" battery maintained a constant LED brightness regardless of severe torsional strain (FIG. 1F), indentations (FIG. 1G), 100% uniaxial stretching (FIG. 1H), and biaxial stretching (FIG. 1I). The example printed battery was shown to withstand high tensile stress without incurring any macrolevel cracking or debonding.

These example images demonstrate the attractive mechanical properties of the example composite ink having the SIS-hyperelastic binder that allows the example rechargeable $ZnAg_2O$ battery to undergo severe mechanical strains without sacrificing device performance. The disclosed technology has particular commercial promise in the field of wearable electronics. For example, many wearable devices require the device to be anatomically compliant and maintain performance during deformations exerted by daily movement of the human body. The use of the example composite stretchable functional materials to formulate printable, stretchable electronics can be implemented for several types of technologies, such as batteries, sensors, actuators, wireless transmitters and/or receivers, and others.

In accordance with some embodiments of the present technology, a method for producing an elastic, conductive ink includes dispersing the copolymer material (e.g., triblock copolymer, such as SIS) in a solvent, e.g., with a similar Hillenbrand solubility parameter, to form an intermediate product, such as a resin. For example, triblock copolymers are typically found as crumbs, flakes, or pellets that will dissolve in the specific solvent to form a resin with a viscosity dependent on the amount of polymer to solvent. Once dissolved, the method includes mixing the utility material, as well as additive materials for certain embodiments, into the intermediate product (e.g., resin) to produce the elastic composite material, such as an elastic conductive ink. The mixing process includes accounting for processing parameters to obtain the final print viscosity of the composite material. In some example embodiments, the method includes producing a printable, stretchable electronics device, such as a wearable stretchable battery, by mixing battery composite powders (e.g., Carbon black, Zn, $Ag_2O$)

as the utility materials into resins of the SIS/toluene. Once thoroughly mixed, e.g., using a Flacktek mixer, the inks can be printed on to a substrate by screen printing to produce the stretchable electronics device.

Example implementations of embodiments of the compositions, devices, systems and methods in accordance with the present technology are described. The example implementations included performance examinations of example composite materials in example embodiments of stretchable electronics devices, such as wearable batteries and sensors, described below.

FIGS. 2A-2E show images and data plots of strain mapping evaluations of example rectangular carbon electrodes formed using the example composite ink. FIG. 2A shows the example rectangular carbon electrodes at 0% stretching for a 1:1 ratio (image A), 1:2 ratio (image C), and 1:3 ratio (image E) and at 100% stretching for a 1:1 ratio (image B), 1:2 ratio (image D), and 1:3 ratio (image F). FIG. 2B shows a data plot of strain versus X position across a fixed Y position for the example rectangular carbon electrodes, plotted over the dotted line. FIG. 2C shows a data plot of the respective resistance monitored during the 10 cycles of 100% stretching iterations. FIGS. 2D and 2E show the respective resistances at release and stretching, respectively. The scale bar in FIG. 2A is 1.0 cm.

In some implementations, a non-contact optical method called DIC can be utilized for strain mapping of the printed carbon electrodes of different SP:SIS ratios (e.g., 1:1, 1:2, and 1:3) upon their stretching. DIC can be employed as a high-resolution imaging tool to analyze the deformations of macroscale objects in real-time to identify faults in materials or design. In these example implementations, the surface is prepared with a white coat and random black speckle, a grayscale intensity pattern can be mapped for each pixel in the digital image of the sample. The incremental displacements of each speckle on the surface can be tracked using this grayscale intensity between images before and after the deformation. Algorithms are used to patch pixels into groups called facets, where strain on the object's surface can be correlated based on the changing dimensions of the facet. The strain ($\varepsilon_x$, $\varepsilon_y$) is calculated by the amount of change in size of the facet (traced by DIC) divided by the original size of the facet. Lower strain value indicates that pixel did not change much in that particular spot. If the pixel does not change much, this indicates that the facet or the location on the sample was hard to deform. Sudden increase in the strain indicates plastic deformations caused by the cracks.

FIG. 2A show images demonstrating a 2D strain mapping ($\varepsilon_x$) of the rectangular carbon electrodes (1:1 ratio, 1:2 ratio, and 1:3 ratio) from 0% stretching (panels A, C and E) to 100% stretching in the x-axis (panels B, D and F). As the electrodes are stretched, there are significant changes in the strain mapping. For all the electrodes, the strain on the textile surface is generally higher than that of the electrode surfaces, as shown by the data plot of FIG. 2B. While a significant drop in the strain is observed at the interface between textile and the electrode, the 1:1 ratio electrode shows the larger drop. Furthermore, the strain distribution on the electrode surface is highly irregular for the 1:1 ratio electrode, and is correlated to the physical cracks of the electrode. Such strain distributions are more uniform for the higher SIS-content electrodes, suggesting that electrodes with higher SIS content are not physically cracked in the optical scale.

In addition to the DIC analysis, change in resistance during the stretching cycles were monitored, shown in FIG. 2C. For example, at stretched state, the 1:1 ratio electrode has consistently high and unstable resistance due to the electrode cracking observed from the DIC (FIG. 2D). For the other two electrodes, with higher SIS content, the resistance values are stable and similar at the stretched state at around 2.3 kΩ. However, when the electrodes are released from the stretching motion, the 1:2 ratio electrode consistently demonstrates the lowest resistance among the three electrodes with 0.65 kΩ (FIG. 2E). In addition to DIC analysis and resistance studies, stress and conductivity of the three composite ratios were simultaneously measured as they were strained. As shown in Table 1 and in FIGS. 9A and 9B, these measurements can compare the Young's modulus, conductivity at 0% strain, conductivity prior to break, and elongation at break. For example, the 1:2 ratio electrode offers the optimum condition among the three composites, with the most favorable tradeoff between relatively high conductivity and a low Young's modulus. This ratio was utilized to fabricate the example carbon current collector electrode for the stretchable $Zn-Ag_2O$ battery.

TABLE 1

Mechanical Characterization of SP:SIS Composite Inks

| Composite SP:SIS Ratios | Young's Modulus (Psi) | Conductivity at 0% Strain (S/m) | Conductivity Prior to Break (S/m) | Elongation at Break (%) |
|---|---|---|---|---|
| 1:1 | — | 60 | 7 | 9% |
| 1:2 | 725 | 44 | 0.68 | 474% |
| 1:3 | 145 | 18 | 0.21 | 598% |

Figure 3:
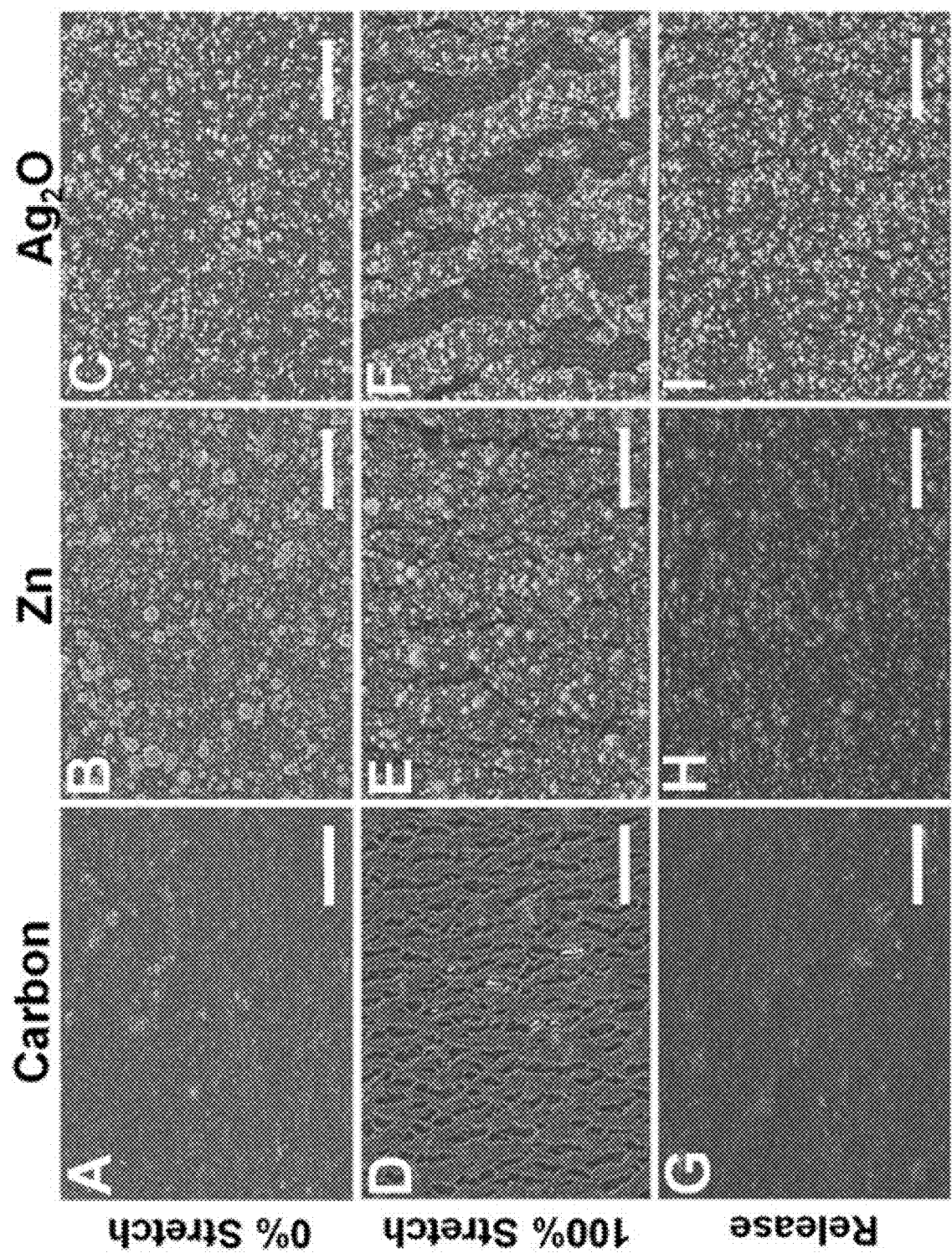
FIG. 3 shows SEM images of the example stretchable $Zn$—$Ag_2O$ battery features as printed, 100% stretched, and released after ten 100% stretching iterations.

FIG. 3 shows SEM images of the example stretchable $Zn-Ag_2O$ battery features, including the carbon current collector (panel A), the Zn electrode (panel B), and the $Ag_2O$ electrode (panel C) as printed; the carbon current collector (panel D), Zn electrode (panel E), and $Ag_2O$ electrode (panel F) as 100% stretched; and the carbon current collector (panel G), Zn electrode (panel H), and $Ag_2O$ electrode (panel I) as released after ten 100% stretching iterations. The scale bar of FIG. 3 is 50 μm.

Although no cracks are observed in the DIC, the resistance still increases upon stretching. Since the DIC can highlight areas of cracking at the macroscale, SEM is utilized to observe physical deformations on the micron scale. Morphology of the optimized carbon electrode, Zn electrode, and $Ag_2O$ electrode were observed before, during, and after stretching. For example, in these example implementations, while no cracks are observed at pristine state, upon stretching, micro cracks were observed. The cracks on these electrodes lead to increase the resistance and limit the electron conduction pathways. Per size of the cracks, carbon electrodes have the smallest cracks compared to those of the Zn and $Ag_2O$ electrodes. For the Zn and $Ag_2O$ electrodes, electrical contacts may be disturbed by such large cracks. For example, the carbon electrode can be kept on the bottom of the Zn and $Ag_2O$ electrodes to maintain the electrical connection. Although the carbon electrode displayed cracks as well, they were minute and uniformly distributed, which allow the electrical connections to be well preserved. After releasing the electrodes following 10 cycles of 100% stretching, both the carbon and Zn electrodes regained their crack-free morphology while $Ag_2O$ displayed only a minor crack.

FIGS. 4A-4D shows data plots depicting the electrochemical performance of the example stretchable battery. FIG. 4A shows a data plot of the first cycle voltage profile of the stretchable battery cycled with 2 mAh cm'. FIG. 4B shows a data plot of the discharge capacity during prolonged cycle, cycled with 3 mAh cm'. Stretching battery was 100% stretched ten times before the electrochemical cycling. FIG. 4C shows a data plot of an electrochemical impedance spectroscopy (EIS) analysis of the pristine state of the example battery. FIG. 4D shows a data plot of an EIS analysis of the example battery stretched to 100%.

As shown in FIG. 4A, the first cycle voltage profiles show high discharge capacity. The pristine battery has 3.78 mAh cm' and stretching battery has 3.94 mAh cm' capacity. Upon stretching, the discharge capacity has slightly increased which is attributable to the enlarged active surface area from the cracks formed during stretching. It is notable that, in these examples, the average voltage decreases after stretching. This decreased voltage may be due to the increased polarization and is more detrimental during the charge. The stretching battery has higher discharge capacity whereas the charge capacity is significantly lower than the pristine. Due to the increased polarization, the second oxidation reaction, $Ag_2O+2OH^-+2e^- \rightarrow 2AgO+H_2O$, from the cathode has not occurred, resulting in lower capacity than the pristine battery during the prolonged cycle, shown in FIG. 4B. However, for both example cases of batteries, the prolonged cycle discharge capacities are stable up to 30 cycles. The first cycle discharge capacity during the prolonged cycle, the pristine has higher capacity close to 3 mAh $cm^{-2}$, e.g., as compared to that of the stretching battery of about 2.5 mAh $cm^{-2}$.

An electrochemical impedance spectroscopy (EIS) was carried out to examine the polarization during the mechanical perturbation. The electrochemical cycling performance of the stretching battery was examined after 10 times of 100% stretching. EIS for the pristine and stretched battery were obtained at pristine state and when the battery was 100% stretched, e.g., in order to understand the difference in polarization of the battery, as shown in FIGS. 4C and 4D. In the EIS, high, medium, and low frequency regions are identified with the light and dark vertical dotted lines in the insets. All three regions have charge transfer resistance and the constant phase elements. The depressed semicircle in the medium frequency region represents the charge transfer resistance of the ions in the electrolyte or the charge of the Zn anode and $Ag_2O$ cathode. The diameter of the depressed semicircle can be used to estimate the charge transfer resistance ($R_2$) on the electrodes. After being stretched, the $R_2$ increases from 115Ω to 540Ω. Before the depressed semicircle, the charge transfer resistance is representative of the uncompensated resistance or the carbon current collector electrode in the high frequency region. The light (left-most) dotted line is used to estimate the charge transfer resistance ($R_1$) of the current collector. After being stretched, the $R_1$ increases from 215Ω to 2400Ω. After the depressed semicircle, the charge transfer resistance is related to the electrochemical reaction in the low frequency region. This highly resistive behavior is commonly observed in the EIS when the spectrum is obtained at the voltage in which electrochemical reaction can occur.

The above example results have illustrated the attractive properties of the example SIS elastomer used as the binder for highly stretchable low-cost screen-printed batteries. As a triblock copolymer (ABA), the example SIS material forms a phase separation of soft isoprene blocks that are physically crosslinked by nanoclusters glassy styrene blocks. This self-assembled elastic network gives SIS superior elastic properties and a lack of a vulcanization step simplifies synthesis of the product. For example, vulcanization is process that crosslinks the polymers, where entropy drives these materials to forcibly retract to their original shape after an applied deformation is removed. This process is unnecessary in synthesis of the elastic composite materials in accordance with the present technology, such as the elastic conductive inks. Also for example, the SIS demonstrated excellent adhesion to substrate, obviating the need for adding non-conductive surfactants commonly used to prevent delamination. For example, the strong adhesion demonstrated by the example synthesized elastic conductive inks can be attributed to the high tack quality of polyisoprene group of the SIS binder. Such ability for imparting stretchability has led to printable batteries that display high performance following multiple severe mechanical strains.

DIC has been shown to be a useful technique to map the tensile strain for the various example stretchable electronic devices composed of different materials and unique compositions. As shown in FIG. 2A, the strain mapping is different between printed traces based on three SP:SIS ratios because of the printed electrodes display a different mechanical behavior that is dependent upon the ratios of inelastic or elastic during the ink synthesis. The interfaces between the materials of different elasticities such as printed electrode and the PU substrate can also be mapped. At the interface, abrupt decrease in the strain is observed for all electrodes. For example, this can be because at the interfaces, the electrode is thickest. For example, when squeeze moves the ink across the cavities of the stencil, most amount of ink is accumulated at the edges. Upon curing, the electrode is thickest at the edges. Because the edges are thicker than the core or outside of the edges, it is harder to displace these regions. To compensate for the low strain on the interfaces, for example, the textiles and thin prints exhibit the higher strains.

For these example implementations using the example printed stretchable battery, the stress and conductivity vs. strain measurements provided additional material characterization of the SP:SIS composites. As shown in Table 1, the example 1:1 ratio composite—as an individual unbound film—demonstrated poor mechanical resilience but the highest initial conductivity. In comparison, resistance measurements on the example 1:1 ratio composite printed on the stretchable Exoskin® substrate demonstrated improved durability, reflecting its behavior as a stiff-island on a soft matrix. The example 1:2 ratio composite exhibits a trade-off of durability and conductivity between the two extreme composite ratios (e.g., 1:1 to 1:3). Such optimal composite behavior is attributed to the engineering of rigid, conductive fillers with elastic polymer binder toward developing highly stretchable inks for specific application. The voltage profiles of the first cycle show that the voltage plateau decreases after stretching, as shown in FIG. 4A. For example, the lower voltage plateau indicates that the polarization increased. However, the SEM images of these example implementations reveal that cracks formed during stretching disappears upon the release, shown in FIG. 3. This discrepancy may be due to the presence of electrolyte. Although the physical cracks may disappear, the electrolyte may soak in between the cracks and hinder the electrical pathway. Furthermore, in these example implementations, the stretched electrode showed the highest areal capacity during the first cycle (FIG. 4A). For example, this may be because the electrolyte has soaked the cracks and has significantly increased the active surface area. When the electrode is stretched, new surface area is exposed and the electrolyte soaks the new surface. The stretched electrodes have the wider active surface area.

In the example EIS results, both $R_1$ and $R_2$ increase upon stretching, as shown in FIGS. 4C and 4D. The degree of rise is significantly different from each other. The $R_1$ escalates by a factor of 11.2 whereas the $R_2$ grows by a factor of 4.70. The $R_1$ is contributed by stretching the carbon current collector electrode and $R_2$ is mostly contributed by the anode and cathode. While both the resistance values increase with respect to the stretching, the $R_1$ increases more significantly. This suggests that the deformations derive the impedance in electric connections more so than the electrodes. If the mechanical strain on the current collector layer can be alleviated, the electrochemical performance can be greatly enhanced. For example, one of the buckling device configurations, a serpentine configuration or cable type of configuration can be employed to alleviate the mechanical strain. Since these configurations can reduce the mechanical strain, the electrochemical performance can be largely improved with intrinsically stretchable electrodes.

These example implementations demonstrate a successful fabrication and operation of a printable, highly stretchable rechargeable Zn—$Ag_2O$ battery based on an example embodiment of the elastic composite material including a hyperelastic SIS as a binder. In the example implementations of the stretchable rechargeable Zn—$Ag_2O$ battery, all the components of the battery were printed using the example high-throughput and inexpensive screen printing method. For example, to obtain the maximum performance of stretchable electronics, systematic and vigorous mechanical studies utilizing DIC and SEM were conducted. The rechargeable Zn—Ag battery was shown to have reversible capacity density of ~2.5 mAh $cm^{-2}$ at 3 mA $cm^{-2}$ discharge current density even after the repeated cycles of 100% stretching iterations. Such performance represents an intrinsically stretchable battery with the highest reversible capacity and discharge current density. The excellent resiliency against severe battery stretching can be attributed to the superior elasticity of the example SIS binder of the composite material, e.g., associated with its long polyisoprene chains with well-spaced, physically cross-linking styrene domains. The first DIC was implemented for localized strain analysis of stretchable electronics, and further optimization of the printed deterministic structures, new materials, and expansion of DIC in the printing design (like the implementation of deterministic structures or sandwich battery designs) have the potential to enhance the electrochemical performance and the understanding of the mechanical properties of SIS-based batteries. The example composite material has the potential to outperform any conventional printed, flexible electronics and is envisioned to pave the way to enhance other forms of energy storage technologies, e.g., including Li-ion batteries, supercapacitors, and photovoltaics towards self-power stretchable electronics. These example SIS-based composite for printed devices can allow several degrees of freedom relevant to a wearer's movement, and can be conformably utilized in diverse real-life situations.

Example embodiments of fabrication methods to produce the example elastic composite inks and example stretchable printed Zn—$Ag_2O$ battery used in the example implementations are described.

Example chemicals and reagents used in the example implementations include Super-P® Conductive Carbon Black ("SP"), toluene (Alfa Aesar), 200 proof Koptec (Decon Labs, King of Prussia, Pa.), Zn powder (Alfa Aesar), $Ag_2O$ powder (Alfa Aesar), $Bi_2O_3$ (Alfa Aesar), and universal mold release (Smooth-On®). KOH, LiOH, polyacrylic acid, and SIS (14% styrene) were obtained from Sigma Aldrich.

The example elastic composite inks were prepared as follows. The elastic carbon current collector ink was prepared by first dissolving 1.10 g of SIS pellets in 5 mL of toluene with analog vortex mixer (VWR) for one hour. Toluene was chosen as the SIS solvent due to their similar Hillenbrand solubility parameters. Then 0.6 g of SP (carbon black) is mixed into the SIS solution in a dual asymmetric centrifugal mixer, e.g., using a Flacktek Speedmixer™, DAC 150.1 KV-K, at 3000 rpm for 5 mins. After cooling the ink, 4 g of yttria stabilized zirconia grinding beads (e.g., 3 mm diameter, Inframat® Advanced Materials) and additional 4 mL of toluene were added and underwent further mixing of 3000 rpm for 30 mins to thoroughly mix and achieve optimum viscosity. The elastic Zn ink was prepared by first dissolving 0.6 g of SIS pellets in 2.8 mL of 80% v/v toluene and 20% v/v ethanol with analog vortex mixer for one hour. Then, 3.4 g of composite Zn powder (30 wt % SP, 60 wt % Zn, and 10 wt % $Bi_2O_3$) were mixed into the SIS solution in the dual asymmetric centrifugal mixer at 3000 rpm for 5 mins. After cooling the ink in air, 2 g of the yttria-stabilized zirconia grinding beads and additional 1.5 mL of the toluene/ethanol solution were added and underwent further mixing of 3000 rpm for 30 mins. The elastic $Ag_2O$ ink was prepared by first dissolving 0.6 g of SIS pellets in 2.8 mL of 80% v/v toluene and 20% v/v ethanol with analog vortex mixer for one hour. Then, 3.0 g of composite $Ag_2O$ powder (20 wt % SP and 80 wt % $Ag_2O$) were mixed into the SIS solution in the dual asymmetric centrifugal mixer at 3000 rpm for 5 mins. After cooling the ink in air, 2 g of the yttria-stabilized zirconia grinding beads and additional 1.5 mL of the toluene/ethanol solution was added and underwent further mixing of 3000 rpm for 30 mins.

The example stretchable Zn—$Ag_2O$ battery devices included the following fabrication processes. The printing process employed a MPM-SPM semi-automatic screen printer (e.g., Speedline Technologies, Franklin, Mass.). The bold "NANO" and rectangle patterns were designed in AutoCAD (e.g., Autodesk, San Rafael, Calif.) and patterned into a stainless steel through-hole 12 inch by 12 inch framed stencils with a thickness of 100 µm (e.g., Metal Etch Services, San Macros, Calif.). A thermoplastic PU sheet (e.g., ST604, Bemis Worldwide, Shirley, Mass.) was thermally bonded to smoothen the surface royal-blue colored high performance spandex (e.g., Spandex World, New York, N.Y.) using a typical drying iron (e.g., T-fal Ultraglide, Parsippany, N.J.). A Keyence VHX1000 optical profiler measured the surface roughness between the ink printed directly on textile and TPU bonded textile.

Figure 5:
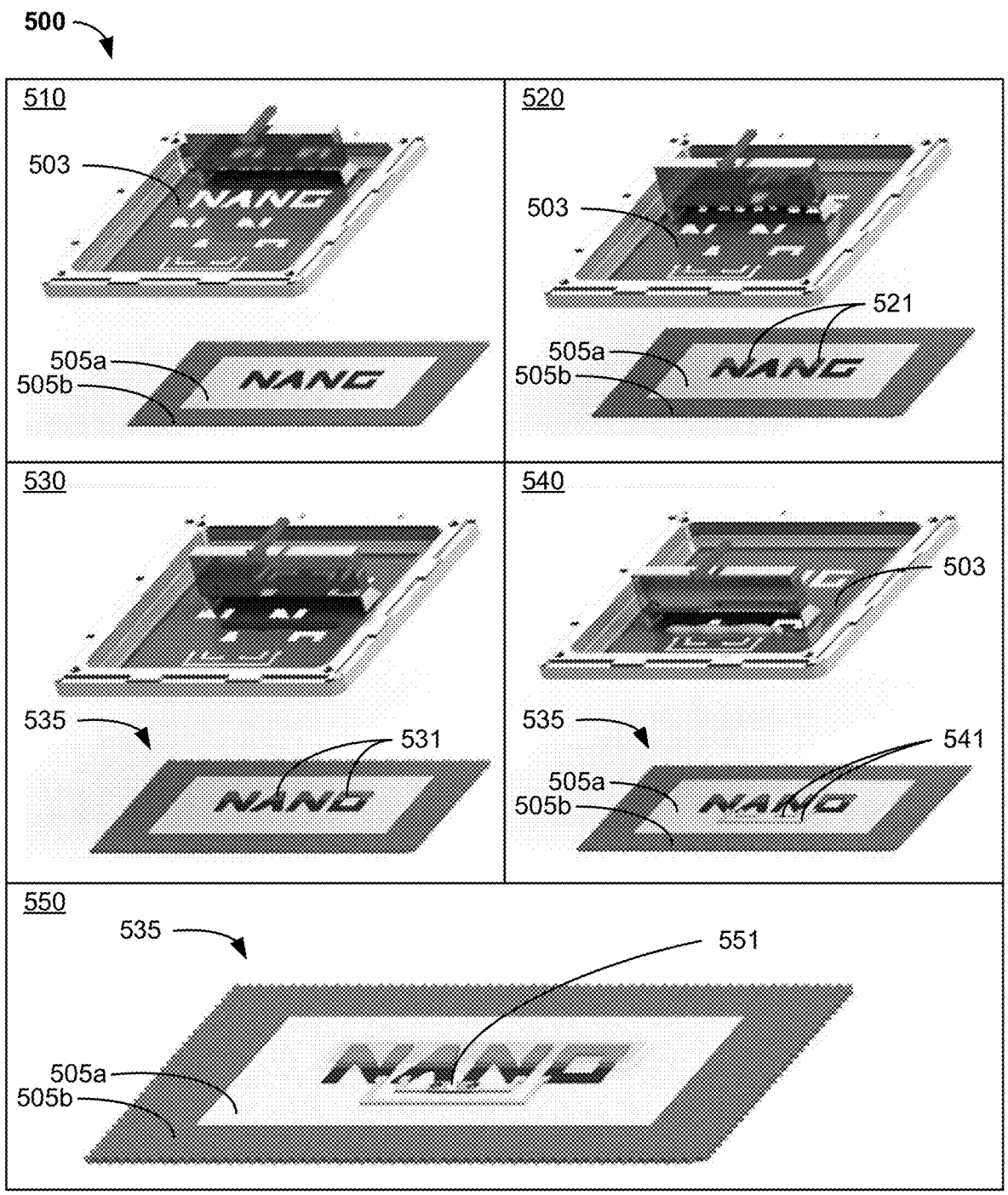
FIG. 5 shows an illustrative schematic of an example fabrication method 500 to produce a stretchable electronics in accordance with the present technology.

FIG. 5 shows an illustrative schematic of an example fabrication method 500 to produce a stretchable electronics in accordance with the present technology. The method 500 includes a process 510 to screen print the example SIS/carbon ink in a desired shape based using a stencil 503 based on a desired stencil design over a substrate 505. In the example shown in FIG. 5, a bold "NANO" design is precut into a stainless steel stencil on the substrate 505, and the example substrate 505 includes a thermoplastic PU sheet 505a that is thermally-bonded to a flexible base substrate 505b, e.g., spandex. For example, the printed SIS/carbon ink can be used to form a current collector component of the stretchable electronics device, e.g., stretchable Zn—$Ag_2O$ battery. In some embodiments, the method 500 includes curing the screen printed ink, e.g., for each ink printing deposition or at least some of the ink printing depositions. After curing the example SIS/carbon ink, the method 500 includes a process 520 to print a stretchable anode 521 (e.g., the stretchable SIS/Zn feature 521 shaped based on the top half of the both letters "N" portions of the stencil 503), and/or a process 530 to print a stretchable cathode 531 (e.g., the stretchable SIS/Ag$_2$O feature 531 shaped based on the letter of "A" and "O" portions of the stencil 503), e.g., by simply changing the stencil position, to produce a printed stretchable electronics device, such as the example printed stretchable battery 535. In some embodiments, the method 500 includes a process 540 to connect the pairs of stretchable batteries by printing a stretchable ink to form one or more other features 541 of the stretchable electronics device, e.g., such as connecting the letter pairs in series by a 3V textile based LED 551. In some embodiments, the method 500 includes a process 550 to produce a protective sheet over certain portions of the produced stretchable electronics device. For example, an electrolyte gel can be applied to each pair separately and heat sealed using a thin PU sheet to prevent leakage and mixing of electrolyte between the pairs. In some embodiments of the stretchable electronics battery 535, the arrangement of the anode 521 and the cathode 531 can be built vertically, in which an electrolyte material is structured between the anode and cathode.

Figure 6:
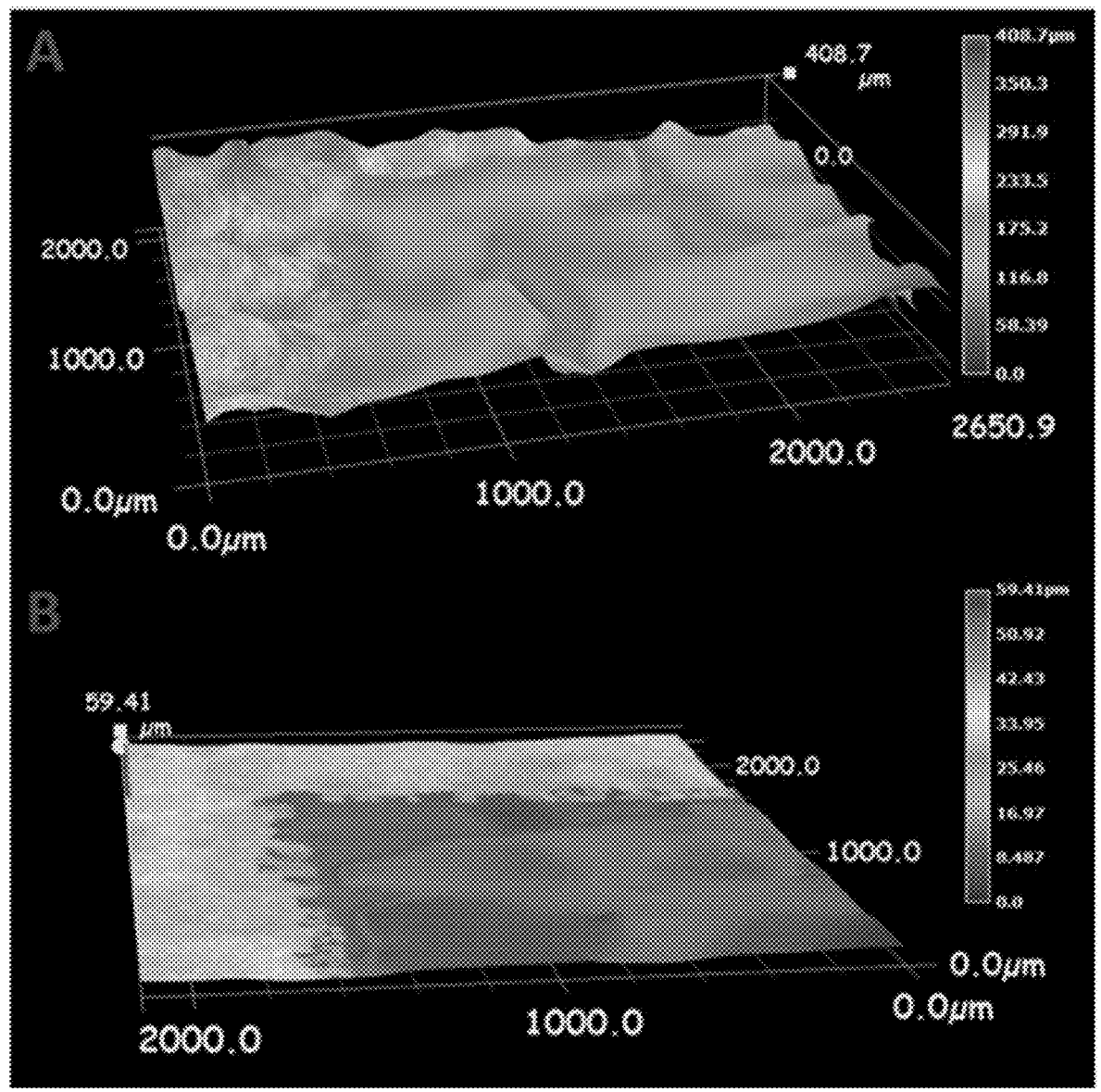
FIG. 6 shows example data using 3D optical profiling of the example printed carbon ink on bare spandex textile and on thermoplastic urethane on spandex textile.

In the example implementations, for example, carbon ink was used to print the entire "NANO" design as the current collector onto a bonded textile and cured in an oven at 80° C. for 15 mins. Subsequently, an anode electrode was printed with the Zn ink on the top half of both letter 'N' carbon prints and cured in an oven at 80° C. for 15 mins. Lastly, a cathode electrode was printed with the Ag$_2$O ink on the top half of the letters 'A' and 'O' carbon prints and cured in an oven at 80° C. for 15 mins. This example design produces two batteries that are connected in series. The outline of the battery was heat-sealed with 26 μm thick PU sheet (e.g., Delstar Technologies Inc. Middletown, Del.). The sealed battery was filled with the electrolyte. The example "NANO" battery design was connected to a textile-embedded 3 V yellow LED (e.g., Lilypad, Sparkfun, Niwot, Colo.). A complete detailed schematic of the device fabrication is shown in FIG. 6.

In some examples of the stretchable battery, an example elastic composite material to produce a carbon current collector component of the battery can include SIS (e.g., copolymer 101) having a % wt in a range of 40%-75% (e.g., 64% wt), and carbon black having a % wt in a range of 25%-60% (e.g., 36% wt), in which toluene is used as a solvent (e.g., 7 mL). In some examples of the stretchable battery, another example elastic composite material to produce the carbon current collector component of the battery can include SIS (e.g., copolymer 101) having a % wt in a range of 40%-80% (e.g., 75% wt), and a graphite-carbon black mix (graphite:SP, 1:0.3) having a % wt in a range of 20 T-60% (e.g., 25% wt), in which toluene is used as a solvent (e.g., 10 mL, e.g., 4 g of SIS in 10 mL toluene).

In some examples of the stretchable battery, an example elastic composite material to produce a zinc anode component of the battery can include SIS (e.g., copolymer 101), and zinc powder. An example formulation of the example Zn anode composite material includes using 3.153 grams of SIS Resin (e.g., 2.4 g of SIS in 11.2 mL (2250 Toluene/550 Ethanol, and 3.593 grams of Zn powder (e.g., 75% Zn, 10% ZnO, 10% Bi$_2$O$_3$, 5% SP). In such configurations of the Zn-based elastic composite material for the anode, for example, the SIS includes a % wt in a range of 10%-40%, and the zinc composite powder includes a % wt in the range of 60%-90%. For example, the zinc composite powder includes Zn, ZnO, Bi$_2$O$_3$, and SP with respective weight ranges of 60-80%, 0.1-15%, 0.1-15%, and 0.1-20% SP.

In some examples of the stretchable battery, an example elastic composite material to produce a silver oxide cathode component of the battery can include SIS (e.g., copolymer 101), and Ag$_2$O powder. An example formulation of the example Ag$_2$O cathode composite material includes using 3.133 grams of SIS Resin ((2.4 g of SIS in 11.2 mL (2250 Toluene/550 Ethanol), and 3.1593 grams of Ag$_2$O powder (e.g., 3003.5 gram of Silver Oxide, 150.2 grams of carbon black (e.g., Super-P)). In such configurations of the Ag$_2$O-based elastic composite material for the cathode, for example, the SIS includes a % wt in a range of 5%-40% and Ag$_2$O composite powder having a % wt in the range of 60%-95%. For example, the silver oxide composite powder includes Ag$_2$O and SP with respective weight ranges of 60%-80% and 0.1%-20%, respectively.

For example, the addition of ethanol can be used for improving the printing the anode/cathode components on to the current collector component. In some example experiments, it was found that a complete toluene solution in the cathode/anode sometimes led to cracks the current collector when printed on top of it. The ethanol addition was shown to reduce the reactive of the solvent, e.g., the Hansen solubility parameter, that allows the ink to be printed on top of the ink with great adhesion and electrical connectivity.

FIG. 6 shows example data using Keyence VHX 3D optical profiling of the example printed carbon ink on bare spandex textile (panel A) and on Bemis Thermoplastic Urethane as smooth interface layer on spandex textile (panel B).

The DIC, SEM, and electrochemical tests were conducted using a pair of 0.9 cm by 3 cm rectangle for the current collector layer and 0.7 cm by 0.9 cm rectangle for the cathode and anode electrodes on a pre-applied PU film commercially named as 9EX-2497P Exoskin® (Dartex Coatings Inc., Slatersville, R.I.).

The example implementations included DIC tensile stress analysis. In these example analyses, carbon current collectors based on three different SP:SIS ratios (1:1, 1:2, and 1:3) were printed on a dog bone shaped cutouts of Exoskin®. The carbon inks were using the same SIS solution as the earlier carbon ink. A while spray paint (e.g., Flat White Prime, Rust-Oluem®, Vernon Hills, Ill.) then a random speckle black pattern (e.g., Flat Black Prime, Rust-Oluem®, Vernon Hills, Ill.) were lightly sprayed on the printed samples. The printed samples were stretched using a motorized test stand (e.g., Mark-10, Copiague, N.Y.) at a constant speed while a pair of high resolution, digital charge coupled device (CDD) cameras was recording a video of the sample from the relaxed to stretched state of 100%. A commercial software GOM ARAMIS (e.g., Trillion Quality Systems, Plymouth Meeting, Pa.) was used to convert the video into single frames for strain mapping. The black speckle on the white coating can create a grayscale matrix per pixel, which tracks the surface displacements of the deformed materials. Mathematical correlation functions are applied to grayscale distribution from the speckle patterns and are analyzed among images before and after the deformation.

The example implementations included mechanical and conductivity characterization of the example SIS composite inks. In these example analyses, three current collector electrodes from the DIC experiment were used to measure the resistance during and after the stretching cycles. The sample preparation was same as the DIC experiment. The stretching tests were conducted on a custom stretching stage of a motorized linear stage and controller (e.g., A-LST0250A-E01 Stepper Motor and Controller, Zaber Technologies, Vancouver, Canada), which is depicted in FIGS. 7A and 7B.

Figures 7A, 7B:
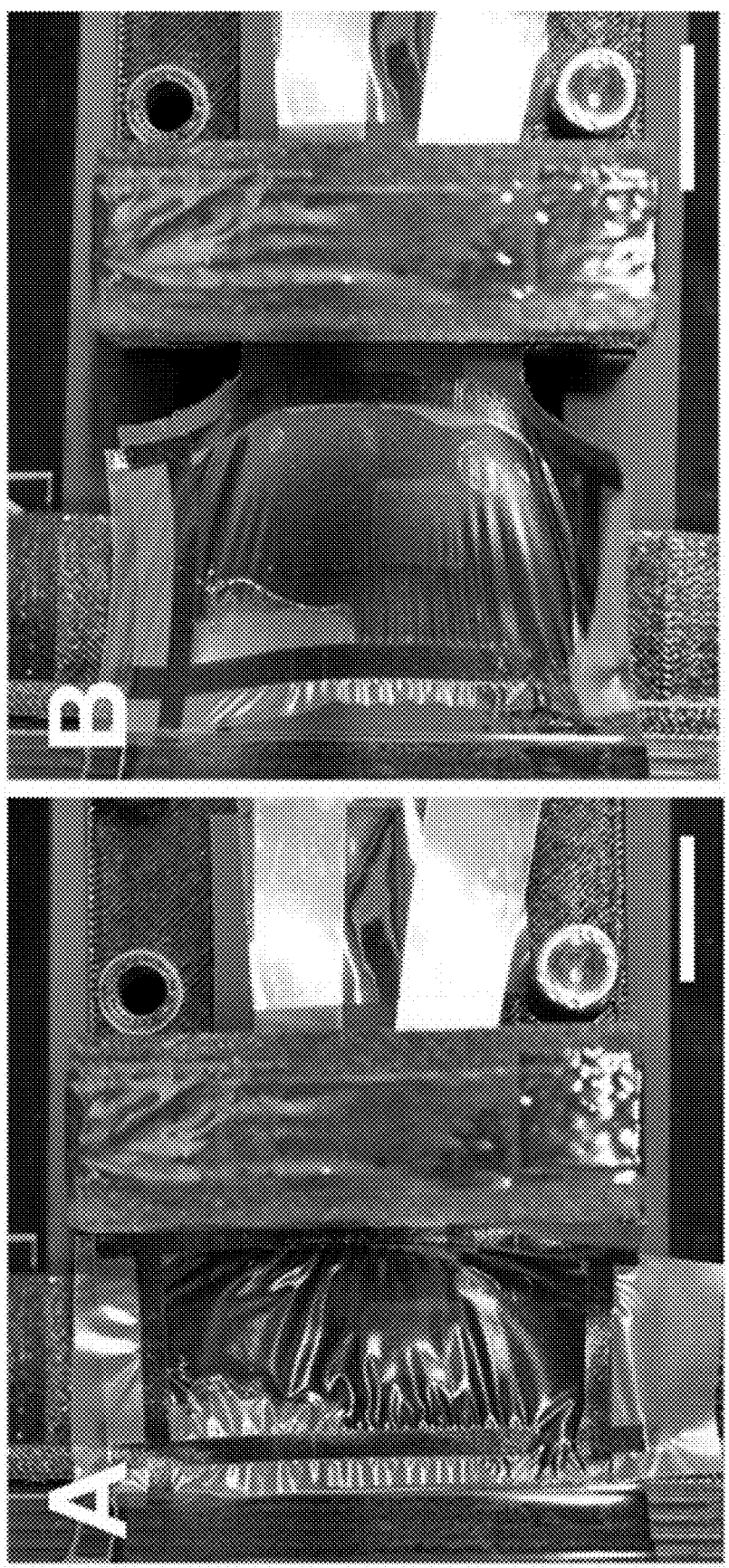
FIGS. 7A and 7B shows images of an example, custom motorized linear stage apparatus from an unstretched position to a stretched position, respectively.

FIGS. 7A and 7B shows images of an example, custom motorized linear stage apparatus from an unstretched position to a stretched position, respectively. The samples were programmed to constantly stretch at a speed of 0.1 cm second$^{-1}$ from 0% to 100% and back to 0% as one cycle. The resistance was measured at 22 pt sec$^{-1}$ using a digital multimeter (e.g., Agilent, Santa Clara, Calif.) during the ten cycles. The speed and length of the physical strain were programmed into a scripting software (e.g., Zaber console, Zaber Technologies, Vancouver, Canada). Additional mechanical characterization of the composites such as Young's modulus, elongation at break, conductivity at 0% strain and conductivity prior to break were conducted. The same composite SP:SIS ratios (e.g., 1:1, 1:2, and 1:3) were prepared by printing on glass slides pre-coated with universal mold release. After curing the samples, the printed samples were easily released from the glass slide and mounted to the custom stretching stage. On one end of the stage, the mount was connected to a digital force gauge (e.g., Mark-10, Copiague, N.Y.) to measure the force applied while the sample is being strained continuously by motorized linear stage. The resistance was measured simultaneously using a digital millimeter. Further calculations based on resistance and force measurements were completed to compare the stress (kN/m$^2$) and conductivity (S/m) of the composite inks as they are strained.

SEM images of the example electrodes included the following. The printed carbon electrode, Zn electrode, and Ag$_2$O electrode were adhered onto a SEM holder. The pristine samples were adhere as printed without any stretching. The stretched samples were adhered with a 100% stretch. The relaxed samples were adhered after the electrodes were repeatedly stretched 100% for 10 cycles. The images were taken using 10 kV energy source using FEI/Philips XL30 ESEM (Philips,).

The example implementations included characterization of the electrochemical properties of the stretchable device. For example, all electrochemical tests were conducted at room temperature. The electrochemical cycling tests were conducting with Arbin electrochemical cycler channels, for example. Electrochemical cycling tests were conducted with 2 mA cm$^{-2}$ first formation cycle and 3 mA cm$^{-2}$ discharge current and 2 mA cm$^{-2}$ charge current for the subsequent cycles. The discharge cut-off voltage was 0.8 V and the charge cut-off voltage was 2.3 V with 20 min constant voltage step. For bending and stretching electrodes, the batteries were electrochemically cycled after being relaxed for 30 mins. The EIS was conducted using a 10$^5$-10$^{-2}$ Hz frequency range with 10 mV amplitude using Solartron 1287 electrochemical interface. All EIS tests were conducted at the open circuit voltage upon the formation cycle.

Other example results using the example printed stretchable Zn—Ag$_2$O battery included the following.

Table 2 shows an example comparison of cycle life, current density, areal capacity, and stretchability of an example embodiment of a stretchable battery with other conventional flexible batteries.

TABLE 2

| System | Cycle Life (80% retention) | Before Stretching | | Stretching | After Stretching | |
|---|---|---|---|---|---|---|
| | | Current (mA cm$^{-2}$) | Capacity (mAh cm$^{-2}$) | | Current (mA cm$^{-2}$) | Capacity (mAh cm$^{-2}$) |
| Conventional Zn—Ag system 1 | 8 | 2 | 1.5 | 11% | 2 | 0.25 |
| Conventional Zn—Ag system 2 | 1000 | 1 | 0.23 | 80% | 1 | 0.18 |
| Conventional Zn—MnO$_2$ system 1 | 4 | 0.33 | 2.2 | 75% | 0.33 | 1.7 |
| Conventional Zn—MnO$_2$ system 2 | 1 | 0.18 | 3.9 | 150% | 0.18 | 3.9 |
| Example Zn—Ag system | 30 | 3 | 3 | 100% | 3 | 2.5 |

Table 3 shows an example comparison of properties including elastic modulus, elongation, and viscosities of elastic binders for stretchable electronics.

TABLE 3

| Elastic Binder | 100% Modulus[1] (psi) | 300% Modulus[2] (psi) | Elongation[3] (%) | Resin Viscosity[4] (cP) |
|---|---|---|---|---|
| Fluorine Rubber (Dai-el G801) | 275 | — | 440 | — |
| Polyurethene (Tecoflex SG-80A) | 300 | 800 | 660 | — |
| Silicone (Ecoflex ® 00-30) | 10 | — | 900 | 3000 (mixed) |
| SIS (Kraton ® D1161, 15% styrene) | 0.1 | 130 | 1300 | 800-1200 (25% w/w in toluene at 25° C.) |

[1]100% modulus: tensile stress at 100% elongation (ASTM D412)
[2]300% modulus: tensile stress at 300% elongation (ASTM D412)
[3]Elongation: tensile elongation corresponding to the point of rupture
[4]Resin Viscosity: initial viscosity of binder, solvent, curing agent (if applicable) prior to adding conductive fillers. Optimal range for screen printing inks is 5000-8000 cP.

Figure 8:
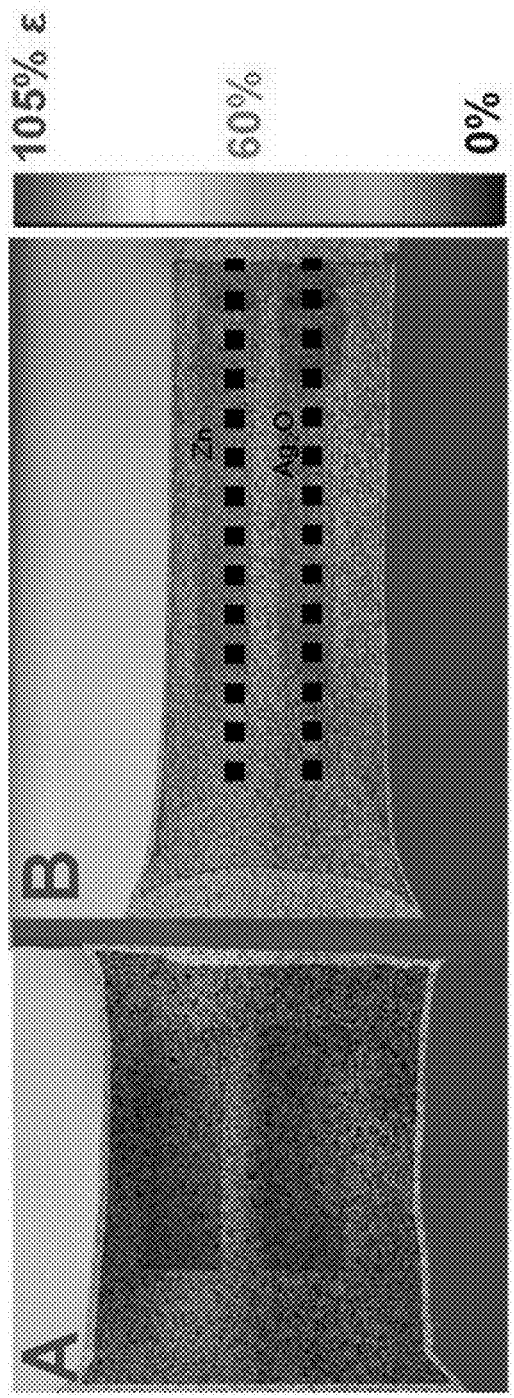
FIG. 8 shows digital image correlation images of example Zn and $Ag_2O$ electrodes printed on top of the optimized carbon electrode before and after stretching.

FIG. 8 shows digital image correlation images of example Zn and Ag$_2$O electrodes printed on top of the optimized carbon electrode before stretching (panel A), and after stretching 100% (panel B).

Figure 9B:
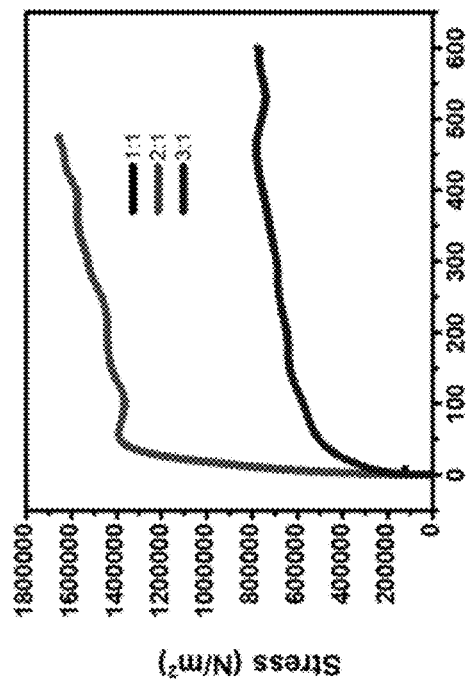
FIGS. 9A and 9B show data plots of conductivity versus strain, and stress versus strain, respectively, of example SP:SIS composites.
Figure 9A:
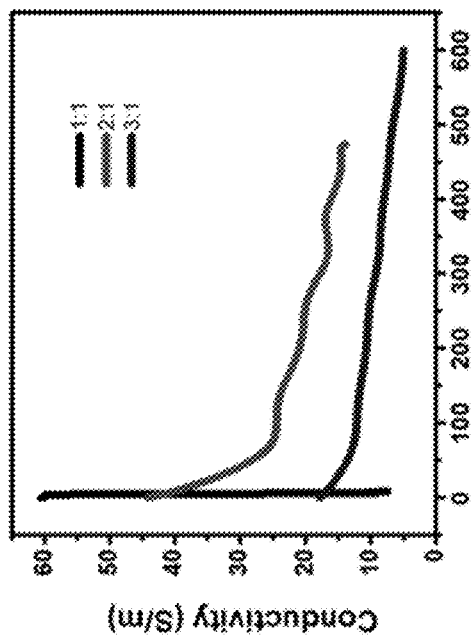

FIG. 9A shows a data plot of conductivity (S/m) versus strain (%) of example SP:SIS composites. FIG. 9B shows a data plot of stress (N/m$^2$) versus strain (%) of the example SP:SIS composites.

Figure 10:
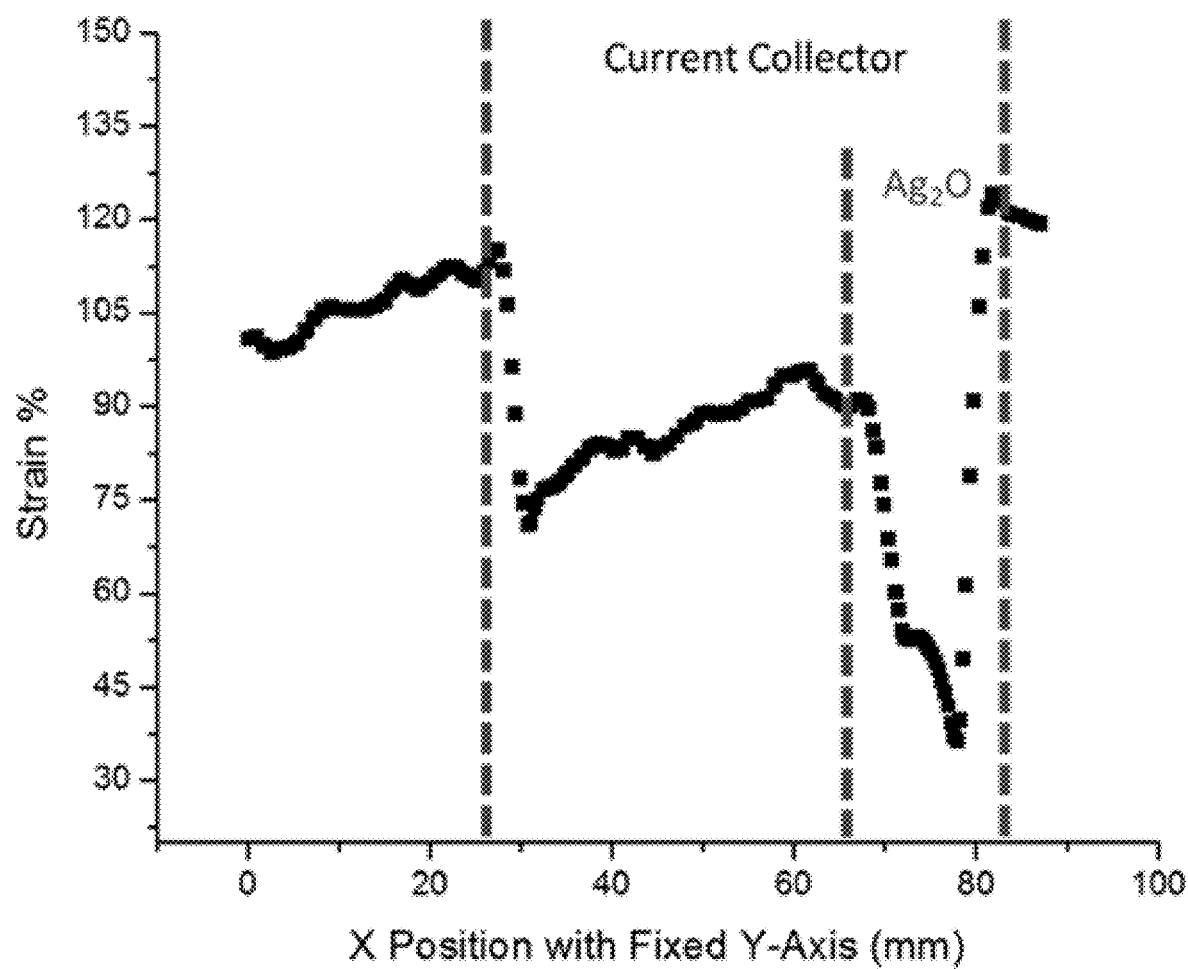
FIG. 10 shows a data plot of strain distribution of an example sample.

FIG. 10 shows a data plot of strain distribution of the example sample, e.g., using the stage shown in FIGS. 7A and 7B, shown over the dotted lines of FIG. 10.

In some aspects, the disclosed systems include stretchable island-bridge (IB) electronics devices and methods of their manufacture. In some implementations, for example, the stretchable IB electronics devices include printable devices based solely on high-throughput screen-printing technology. The stretchable IB electronics devices include stress-enduring, composite inks formed in a "island-bridge" design, such that the devices can be applied to both skin-worn and textile-based applications. These devices can employ thick-film fabrication techniques to incorporate a wide-range of materials and designs, thereby enabling new directions for stretchable electronics that were not possible before. Example advantages and practical utilities of the disclosed stretchable IB electronics devices and fabrication methods are described, including example implementations of a wearable zinc battery as an example. For example, by enabling cheaper processing alternatives and a utilization of unlimited materials, stretchable electronics are envisioned to replace current state of rigid, bulk electronics and continue the ubiquitous of electronics on skin, robotics, and clothing.

After a decade of smartphones and wearable products proliferating into every aspect of our daily lives, the drive for smaller, thinner, and more conformal electronics has invoked a shift in the electronics industry. A new generation of electronics, such as sensors, e-textiles, soft robotics, wearable electronics, energy storage devices, and hemispherical eye cameras, are being engineered to fit and flex with the surfaces they attach to or interface with so that they become indistinguishable from that object, such as skin, clothing, etc. Designs that enable the electronics to conform and deform move with its attached structure are referred to as "stretchable electronics." This new class of electronics relies on its ability to seamlessly mate with curvilinear surfaces while maintaining stable performance, even under extreme strain is applied. This enables novel form factors that were not possible with conventional electronics.

The fabrication of stretchable electronics has generally relied on modifying composites via the following approaches: deterministic design and intrinsic materials properties. The deterministic design approach turns geometrically patterned, traditionally rigid materials into device where extremely thin, serpentine-/coil-shaped interconnections, known as the "bridges" are integrated to accommodate strain between non-deformable parts, usually the functional components known as "islands" and binds them onto a soft, stretchable substrate. The deterministic design approach offers some advantage since the functional components do not intrinsically stretch, but can maintain consistent performance when being stretched. Stretching can be achieved through in and out of plane buckling using selective bonding of islands to the substrate. Fabrication of this class of electronics devices typically use subtractive, lithographic fabrication methods that are extremely expensive and low-throughput. Moreover, this class of devices are limited to a small list of materials compatible with the fabrication techniques, in addition to an expensive and complex, time-consuming fabrication steps.

Alternatively, the intrinsically stretchable class utilizes conducting polymers where their molecular structures can be fine-tuned to enable stretchability. The properties of conductive polymers through solution processing presents a more cost-effective approach than deterministic design approaches. Unfortunately, the use of conductive polymers are still inferior electronic and semiconducting properties compared to bulk metals and semiconductors.

Example embodiments and implementations of the disclosed stretchable IB electronics devices, systems and methods are described. The example implementations included performance examinations of example composite materials in example embodiments of stretchable electronics devices, such as wearable batteries and sensors, described below.

FIGS. 11A-11K shows example embodiments of a stretchable island-bridge (IB) electronics device platform and a fabrication method in accordance with the present technology. The example stretchable IB electronics device platform includes deterministic structures suitable for epidermal or textile applications. For example, the all-printed IB structure are formed using printing techniques and creative integration of elastic composite inks and deterministic patterning. Example methods of depositing inks on to surfaces makes capable the printing of colorful, artistic designs for temporary tattoos, textiles, and electrochemical devices, such as for glucose monitoring, because of its affordability, high-throughput, and simplicity. In the examples described herein, the design of the conductive ink formulation includes a block-polystyrene-block-polyisoprene-block-polystyrene (SIS) copolymer, which acts as a hyperelastic binder that provides the ink product with superior mechanical performance. In the produced elastic composite ink, the block-polystyrene part of polymer chains formed a physical cross-linking e.g., due to the affinity of styrene to each other, while all the block-polystyrene crosslinking center were interconnected by long chains from the block-polyisoprene. As such, a self-assembled hyperelastic nanostructure of "nanoislands" connected by "nanobridges" can be formed using the elastic composite ink. The fabrication method employed to produce the example stretchable IB electronics device can solely utilize thick-film printing to form both the island and bridge structures. In the example implementations described below, particular attention in printing the stretchable serpentine silver interconnects is paid to the sinuous geometry (e.g., line width or angle), the observed performance of the fabricated device, and the interface of the printed serpentine bridges with the printed functional composite islands.

For example, integration of the elastic composite materials with a deterministic design approach of structural components provides an extremely versatile technique to produce stretchable electronics, e.g., by embedding any type, or combination of conductive fillers into an elastic matrix to form an elastic, conductive composite. Employing elastic composite materials is an attractive approach for its versatility, as electrical and elastic performance can be tailored based on the ratio of composite materials. In addition, the unlimited number of material choices, such as nanomaterials of various morphological shapes, are already seeing massive implementation in various technologies and disciplines, and can be easily incorporated in this process. The scope and limitations of the new printing strategy are discussed and demonstrated below in the examples below. One example shows the practical utility of the disclosed technology illustrated in a skin-worn, printed zinc battery with an area density capacity of 1.6 mAh/cm$^{-2}$.

Example fabrication of "Island-Bridge" stretchable electronics device is as follows. As stretchable electronics continue to evolve from rigid technologies listed previously, it is imperative for the fabrication to be versatile applied on to any substrates compatible with particle-polymer composites. This becomes particularly challenging for epidermal and textile-based electronics that demand these devices to be inexpensive and scalable. These requirements, combined with the rise in complex nanomaterial composites, will present unlimited possibilities for inexpensive, high-performance and stretchable electronics.

Figure 11A:
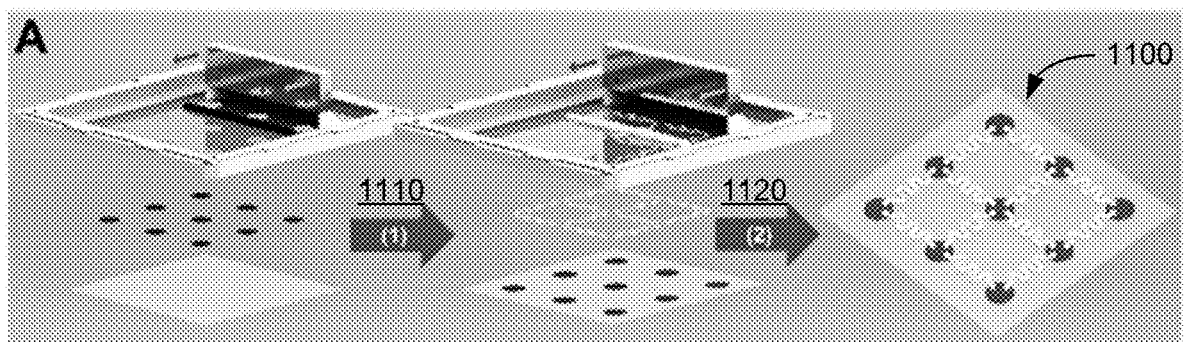
FIGS. 11A-11K shows example embodiments of a stretchable island-bridge (IB) electronics device platform and a fabrication method in accordance with the present technology.

FIG. 11A shows an illustrative diagram depicting an example screen-printing, fabrication method to produce a stretchable IB electronics device using elastic carbon ink as functional islands and followed by elastic, silver bridges in a serpentine configuration (e.g., line width greater than 150 microns). FIGS. 11B-11J show images depicting features of an example stretchable IB device, during fabrication. FIG.

Figure 11K:
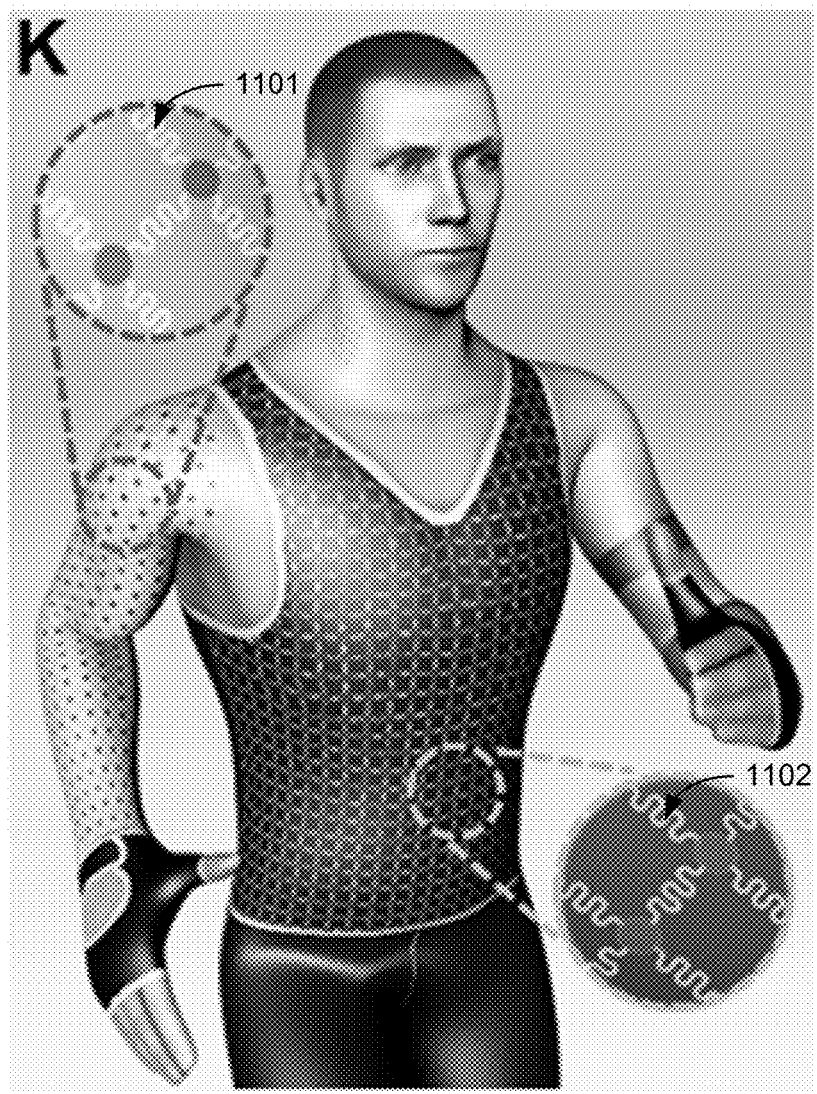

11B shows the printed elastic carbon ink on water-soluble tape. FIG. 11C shows an elastic, serpentine bridge printed on top of carbon. FIG. 11D shows a sample of the device after curing, which can be transferred to skin and have the water-soluble tape removed with a simple washing step. FIG. 11E shows the printed sample transferred on to skin. FIG. 11F shows the sample of FIG. 11E zoomed in. FIG. 11G shows the sample being compressed on the skin. FIG. 11H shows an example printed island-bridge directly produced on a textile. FIG. 11I shows the sample of FIG. 11H zoomed in. FIG. 11J shows the sample being folded on the textile. FIG. 11K shows an illustration depicting an example use of these stretchable IB electronics devices that can be expanded for large-area electronics on skin and textiles.

As shown in FIG. 11A, a 3 by 3 array of functional islands connected with serpentine bridges were fabricated in two processes by example screen printing techniques. The fabrication method shown in FIG. 11A includes depositing inks, including example elastic composite inks, on to surfaces. For example, the method can include utilizing a computer-aid design (CAD) software, such that any desired design can be patterned into a custom designed, stainless steel stencil to control where the ink is deposited onto a substrate. The method includes a process 1110 to print one or more elastic composite materials 100, e.g., any engineered ink composite of any desired conductive filler and polymers in accordance with the present technology, such as an elastic/graphitic ink, on a substrate using a stencil to form functional islands. The method includes a process 1120 to print one or more elastic composite materials 100 to form bridge structures, e.g., in the form of serpentine interconnects, to link the islands on the substrate, to produce the stretchable IB electronics device 1100. For example, the wide variety of substrates are readily adaptable to printing technologies such as a water-soluble tape that can be used to aid in the device transfer onto the epidermis or directly on top of a textile.

Figure 11B:
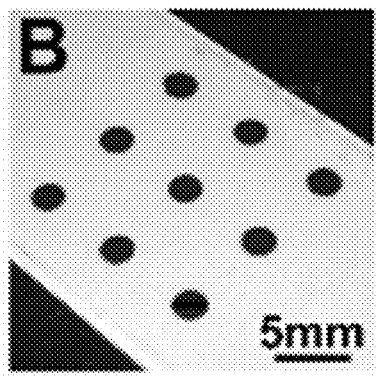
Figure 11C:
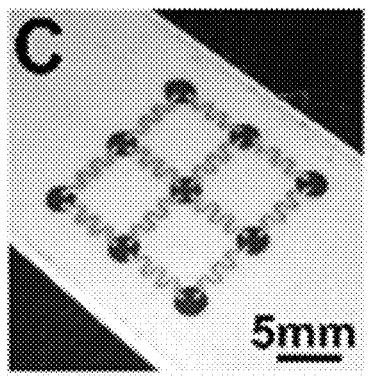
Figure 11D:
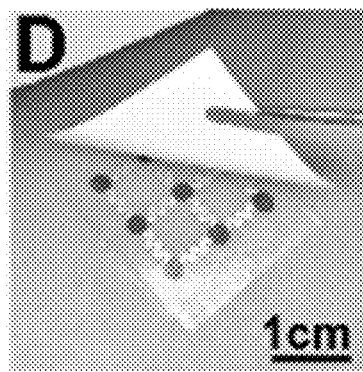
Figure 11E:
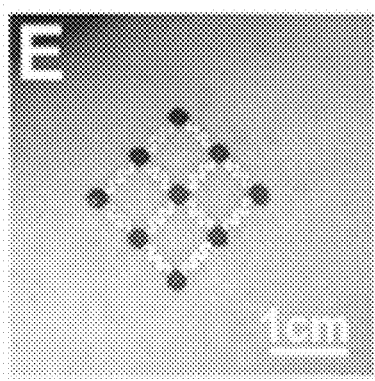
Figure 11F:
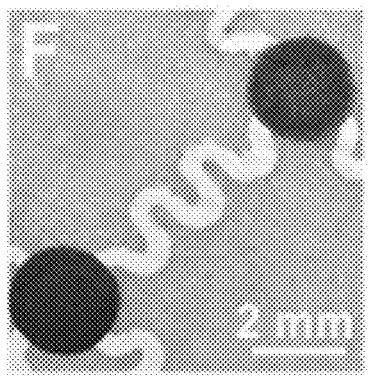
Figure 11G:
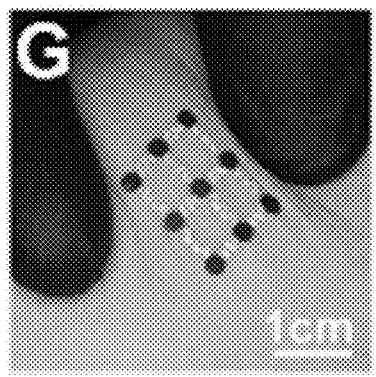
Figure 11H:
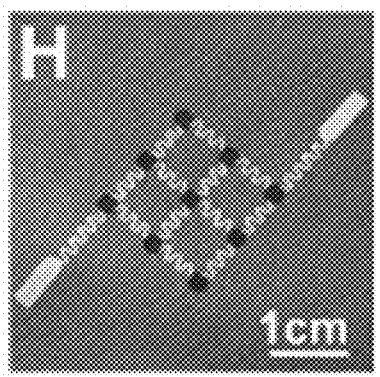
Figure 11I:
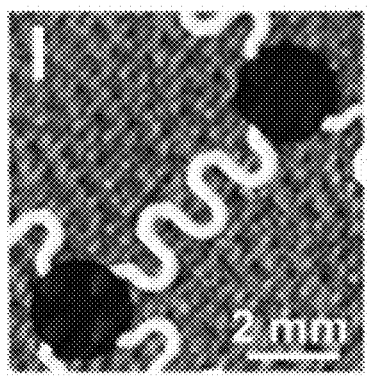
Figure 11J:
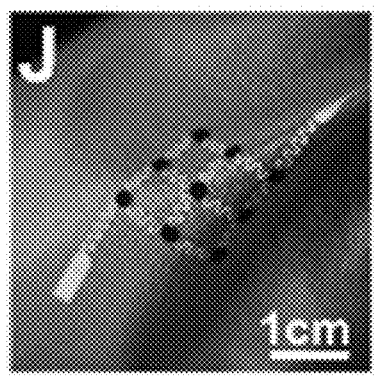

The example shown in FIG. 11B of the printed elastic carbon ink on a water-soluble tape included, after subsequent curing of the first printed layer, mixing a highly conductive Ag-flake (e.g., 2-4 micron) with a resin of the elastic polymer in organic solvents to produce the desired elastic composite ink. The elastic composite ink was printed directly on top in a specific serpentine, therefore acting as an elastic bridge between the functional islands, shown in FIG. 11C. Thorough analysis of each component's purpose in the ink was used for optimization of the composite's elastic and conductive properties, discussed later in further detail.

After curing the printed inks on to a water-soluble tape, the tape can be peeled from the carrier paper, flipped and attached onto skin that is pre-coated with a medical adhesive, as shown in FIG. 11D. For example, after applying considerable pressure to ensure adhesion, the water-soluble tape was rinsed off gently with water in less than 30 seconds. The example printed device remains on the skin with a high resolution without residue of substrate, and is capable of undergo multiple forms of deformation such as compression, pinching, indentations, as depicted in the images of FIGS. 11E, 11F and 11G. By reversing the printing order, for example, the device can be printed directly on to the surface of a textiles, where both island and bridges can undergo the same deformations, as depicted in the images of FIGS. 11H, 11I and 11J. The diagram of FIG. 11K shows an example of a user employing the printed stretchable IB electronics devices on body, e.g., stretchable IB electronics device 1101 attachable directly on epidermis or stretchable IB electronics device 1102 attachable on textiles, robotic skins or other interactive, curvilinear surfaces, in which the used can be partially or completely covered with stretchable electronics, e.g., due to the simplistic and versatility of this fabrication large-area electronics, textiles.

The formulation of the elastic inks is important to achieve great contact with a rough surface of the skin. One example of the elastic composite material 100 includes the triblock copolymer SIS, in which the elastic composite material in the stretchable IB electronics device can achieve stretching with high elongation, e.g., greater than 1500%. In example implementations, the elastic conductive ink using SIS demonstrated very high stretchability while being able to bind a significant amount of conductive filler such as silver flake or carbon micron powder in the ink formulation. The unique elastic structure of SIS includes both elastic blocks and plastic blocks which self-assemble into a network of physical crosslinks which attributes to the high stretchability of the polymer. The serpentine bridges easily adhered to the cervices and hills of skin even at the interface of the island-bridge, even when stretched or twisted of the skin.

FIG. 12A shows a diagram showing geometric parameters for width, length, and angle of example serpentine bridges used in example embodiments of the stretchable IB electronics devices. The example serpentine bridges are composed of unit cells, e.g., a "horseshoe" design, where its arc width (w) (e.g., >50 microns), arch radius (e.g., 10-45°), arc angle ($\theta$) (e.g., 0-1000 microns), and linear arm (l) connecting unit cells can be varied to determine the stretchable properties. For example, these features can be specifically designed using a computer-aided design (CAD) software to be cut into a stainless stencil for screen printing.

FIG. 12B shows an image of a stencil employed for printing electronics of pre-cut design. FIG. 12C shows an image of stencil design for serpentine bridge with varied line width (e.g., w=150, 250, 500 micron/um). For initial tests, the length of the linear arm was varied (e.g., 0, 500, and 1000 microns), as shown in the section of the stencil. These unit cells can create complex mechanical behaviors due to their different dimensions and FEA modeling can be used to predict its stretchability, and the addition of elastic polymer will additional degree of stretchability. A single straight line denoted as S and three serpentine designs with the increasing linear arm length are identified in order as, 2, 3 are printed on PU and stretched from 0% to 100% over multiple iterations. FIGS. 12D and 12E show optical images of printed, stretchable inks using varied serpentine design at 0% stretch (FIG. 12D) and 100% stretch (FIG. 12E). FIG. 12F shows a zoomed image providing a closer look at a single, extended serpentine turn, showing high quality and resolution of the print that has no noticeable cracks even under deformation. The adhesion to the PU is evident as well, with no signs of delaminating especially at the linear arms, which undergo most of the strain.

FIGS. 12G and 12H show data plots depicting the change of resistance as each printed design is stretched 100% (FIG. 12G) and tested for 10 cycles of repetitive stretching (FIG. 12H). The measurement show the resistance of each device while being strained at a constant speed. For example, the three serpentine designs all demonstrated a superior stability of their change of strength compared to the straight line when being stretched 100%. Interestingly, the pattern of serpentines using the elastic composite ink provided different properties as compared to conventional serpentine designs using conventional materials, which showed that increasing the linear arc angle will typically result in better durability. For example, this distinction was attributed to nature or thick-film screen-printing where the deposited ink was bound tightly to the substrate. The tight binding is individually designed in the ink formulation, so the delamination of printed composites from the substrate during flexing and stretching can be avoided. The solvent used in the ink, e.g., toluene in this case, can partially react with the substrate and cause partial dissolution/swelling of the substrate material, hence allow the ink composite to strongly bond to the substrate after the solvent is evaporated. However, as a tradeoff, when the IB structure is being stretched, the serpentine is unable to isolate itself from the substrate, hence being internally expanded along with the substrate. The expansion of the composite can cause the resistance of the serpentine to increase. While this can be partially overshadowed by the serpentine design, data from the example stretching tests show the larger difference as linear arm length. Initially, as the linear arm length increases, the electrical conductivity becomes increasingly stable. However, above a certain length, the expansion of composite becomes the dominant factor of the resistance of the serpentine due to the extra linear arm length. Moreover, from a practical manufacturing angle, as the linear arm length increase, the occurrence of defects increases, as this location of the stencil is often more fragile, and the complete pattern becomes harder to print. This anomaly can be attributed to the fine resolutions (e.g., less than 250 µm) of these prints and that is tightly bonded to the substrate thus being stretched laterally as well. This may be attributed to why, for example, line 3 with the 1000-micron length, had demonstrated relatively less durability as compared to the 500-micron length. Since the extended linear arm is perpendicular, the longer the length can exhibit stretching of its line width, which may cause deformation in the printed composite ink. This example result is evident from the example cycling test shown in FIG. 12H, where line 2 also demonstrated a superior durability compared to the straight line and other serpentine designs.

Figures 13A, 13B, 13C:
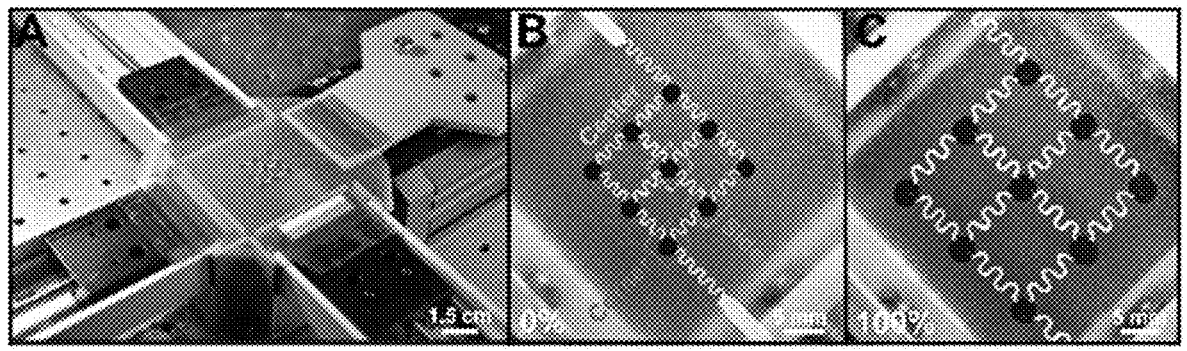
FIGS. 13A-13I show images and data plots pertaining to evaluation of example island-bridge designs of example embodiments of stretchable IB electronics devices.
Figures 13D, 13E, 13F:
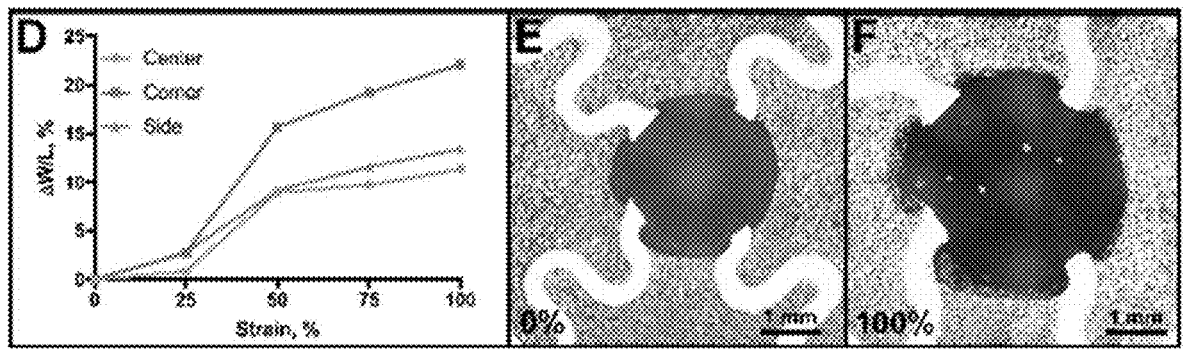
Figures 13G, 13H, 13I:
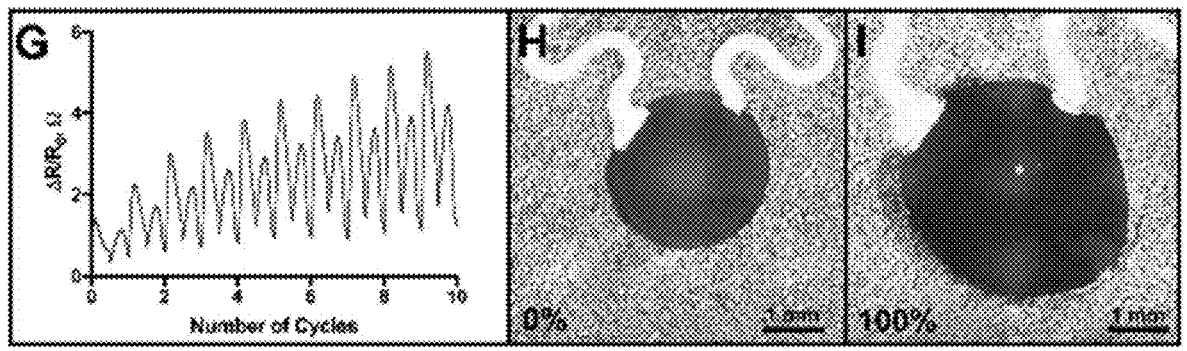

FIGS. 13A-13I show images and data plots pertaining to evaluation of example island-bridge designs of example embodiments of stretchable IB electronics devices. FIG. 13A shows an image of a sample mounted onto a custom-made, motorized stage. FIGS. 13B and 13C show images of a unstretched sample and stretched sample of 3 by 3 island-bridge array with designed imaging of island deformation, respectively. FIG. 13D shows a data plot depicting the deformation of islands at different island-serpentine pairs stretched from 0% to 100%. FIGS. 13E and 13F show microscopic images of center island at 0% stretch (FIG. 13E) and 100% stretch (FIG. 13F). FIG. 13G shows a data plot showing example conductivity measurements of biaxial stretching to 50% over 10 cycles. FIGS. 13H and 13I show microscopic images of corner island at 0% stretch (FIG. 13H) and 100% stretch (FIG. 13I).

The remarkable stretchability of the example serpentine designs using the example elastic composite materials and screen-printing technologies were studied in conjunction with functional islands. For example, unlike deterministic approaches that rely on serpentine bridges to accommodate all the strain, these example printed "island-bridge" can exhibit both the serpentine and functional islands stretch when strained is applied. In an example evaluation using custom, mechanical stretching stage, for example, an elastic composite ink composed of silver flake and SIS was printed in a serpentine design onto polyurethane as followed by an elastic ink formulation consisting of super-P and SIS, shown in FIG. 13A. In the example design, there are different number of serpentine bridges connected to a specific bridge, such as the "side", "center", and "corner" designated in FIG. 13B. From a macro perspective, the complete device stretching is shown with uniformity, e.g., despite the difference of serpentine connections that could add additional strain or the risk of delamination, as illustrated in FIG. 13C.

When the functional islands were evaluated at a microscopic level, non-uniform expansion was noticeable, e.g., when compared to the "center" island. In FIG. 13C, the ratio of cross-sectional diameters should have a consistent ratio of 1, for example, to maintain the circular shape, but this was only demonstrated with the "center" island. This example demonstration by the center island included stretching from 0% stretch (FIG. 13E) and at 100% stretch (FIG. 13F). The other "corner" and "side" islands exhibited higher strain along the lengths of the serpentine connections, reflecting the formation of an elliptical shape when strained from 0% (FIG. 13H) to 100% (FIG. 13I). Also, for these example implementations, pinholes were visible in the carbon ink at the interfaces between the PU substrate, carbon island, and silver serpentine bridge when the ink is stretched. Since the "island" components require higher loadings of conductive carbon fillers to compensate for their low conductive compared to the stretchable silver, serpentine, the carbon "island" is shifted more in proportional of the silver ink. This may cause the example carbon island to form pinholes, delamination around the connection site, and disproportional deformation at different sits of the array. This presents an exciting aspect as compared to lithographic structures.

In some example embodiments, the example stretchable electronics devices can include intricate designs or arrangements of the array "island-bridge" array, e.g., using triangular, hexagon, and many more geometrical structures between the stretchable island/bridge configuration, which can present new types of behavior, e.g., especially evaluating the depth of the connection. These example different designs may change the amount of surface area is available for functional islands, e.g., as the IB array sacrifices active area to provide more durability.

Figure 14A:
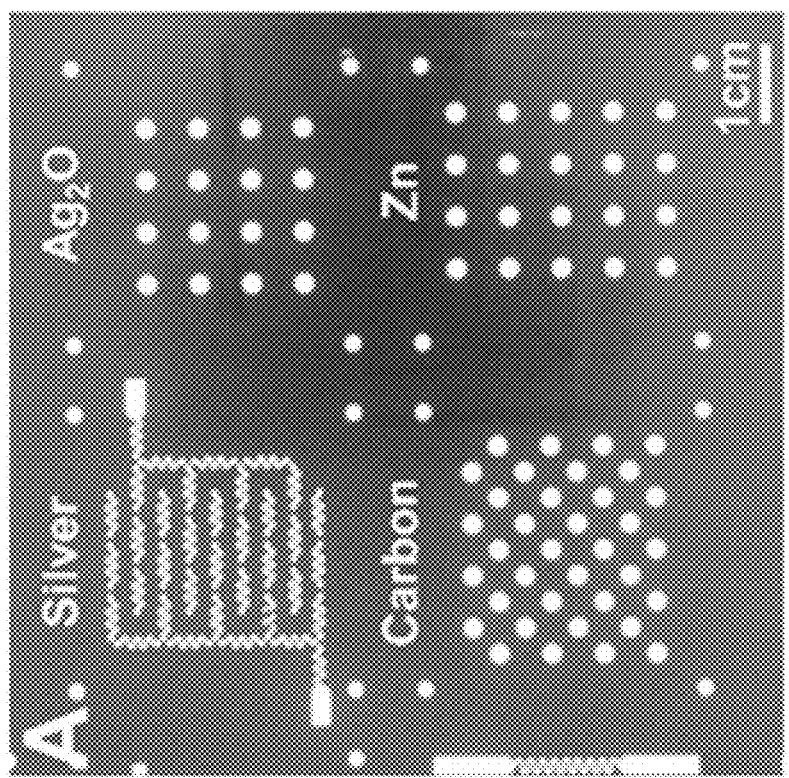
FIG. 14A-14E show images, illustrations and data for example embodiments of a printed stretchable island-bridge zinc-silver oxide battery.
Figure 14B:
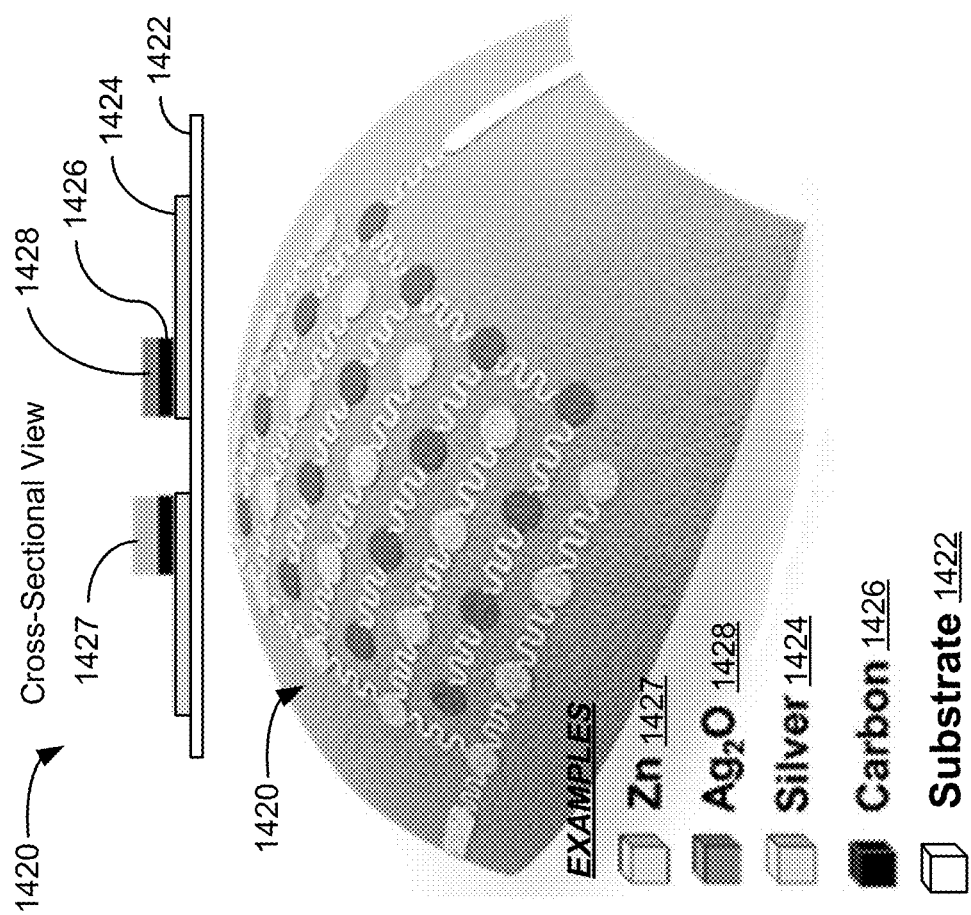
Figure 14C:
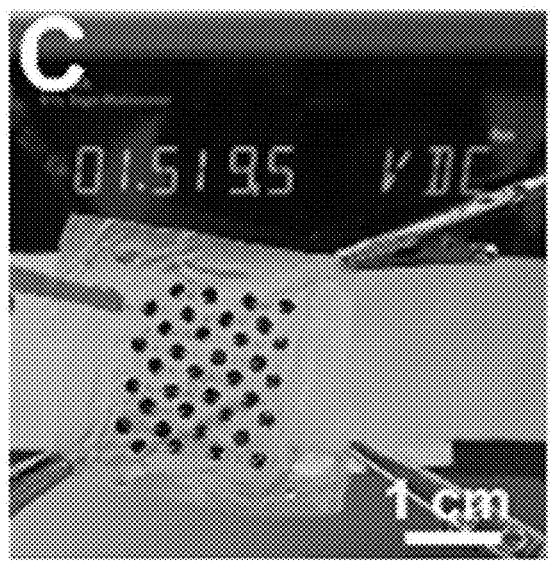
Figure 14D:
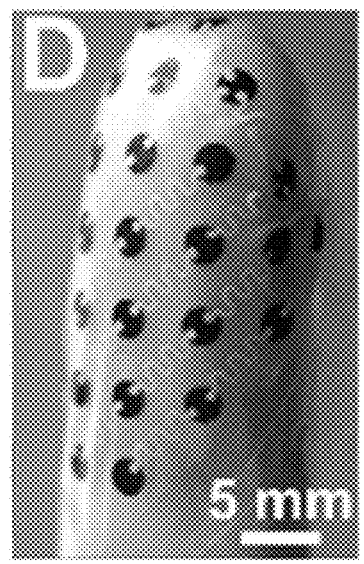
Figure 14E:
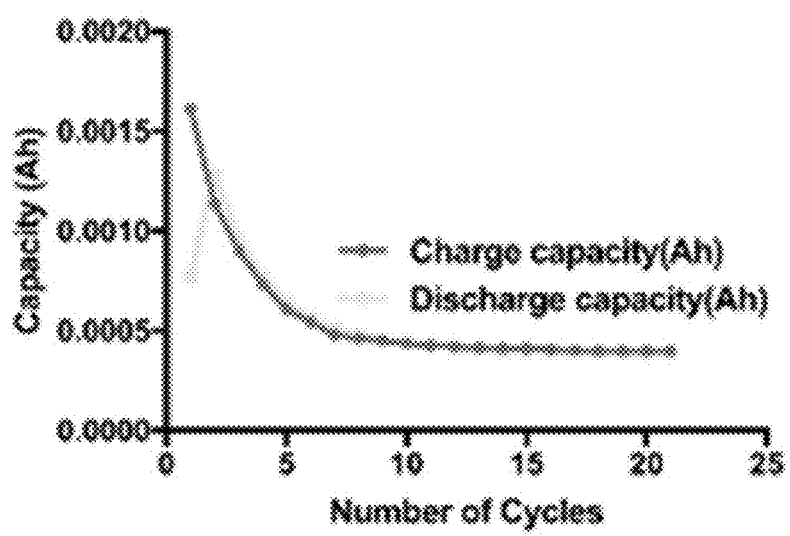

FIG. 14A-14E show images, illustrations and data for example embodiments of a printed stretchable island-bridge zinc-silver oxide battery. FIG. 14A shows an image of an example stencil design for a serpentine bridge that can be employed in the example stretchable IB zinc-silver oxide battery. FIG. 14B shows an illustrative diagram depicting an example epidermal energy storage device, e.g., a stretchable, rechargeable IB zinc-silver oxide battery 1420, conforming to skin in an interdigitated design of island-bridge. FIGS. 14C and 14D show images of an example final print of the stretchable battery and its voltage output (FIG. 14C) and of the final printed stretchable battery surrounded around an index finger of a user. FIG. 14E shows a data plot depicting the charge and discharge curves for the example rechargeable battery.

As shown in FIG. 14B, the stretchable, rechargeable IB zinc-silver oxide battery 1420 includes a stretchable substrate 1422 including an elastic and electrically insulative material structured to conform to an outer surface of an object, e.g., such as skin, textile or other material surface of any object. The stretchable, rechargeable IB zinc-silver oxide battery 1420 includes a layer of a conductive material that forms the island-bridge structure 1424, e.g., which can span in one or more directions on the substrate 1422. In some examples of the battery 1420, the island-bridge structure 1424 includes silver. The stretchable, rechargeable IB zinc-silver oxide battery 1420 includes an underlayer of a conductive material on a particular region over the island-bridge structure 1424 to form a current collector structure 1426. In some examples, the current collector structure includes carbon black (e.g., SP). In some embodiments of the battery 1420, the current collector structure 1426 is patterned in an array over various portions of the island-bridge structures 1424, which can include in the manner shown in the example design depicted in FIG. 14B. The stretchable, rechargeable IB zinc-silver oxide battery 1420 includes an anode structure 1427 formed over at least one of the current collector structure 1426. The stretchable, rechargeable IB zinc-silver oxide battery 1420 includes a cathode structure 1428 formed over at least another one of the current collector structure 1426. Various designs of the stretchable, rechargeable IB zinc-silver oxide battery 1420 can be produced such that one or more anode structures 1427 are arranged to be separated and proximate one or more cathode structures 1428. In some embodiments of the stretchable, rechargeable IB zinc-silver oxide battery 1420, the arrangement of the anode structure 1427 and the cathode structure 1428 can be built vertically, in which an electrolyte material is structured between the anode and cathode.

The example design of the island-bridge structure shown in FIGS. 14A-14D is quite adaptable to various technologies, e.g., especially for electrochemical devices such as batteries, biofuel cells, supercapacitors, and chemical sensors that require two opposing electronics. The results of the example implementations shown in FIGS. 14-14E demonstrate the applicability of the printed "island-bridge" for a printed battery using the disclosed elastic composite materials. The individual engineered inks are synthesized for zinc and silver-oxide electrodes using the example copolymer and powder composites of active material, conductive additives, and/or other metals to improve the rechargeability of the desired product. For example, zinc chemistry was selected for its safety and ability to print in the air, but essentially any battery chemistry can be applied to this format. The island-bridge array was modified into an interdigitated design of zinc anode and silver (II) oxide cathode, shown in FIG. 14A, e.g., demonstrating the reaction in shown in FIG. 14B. The example silver serpentine connections were printed first onto a polyurethane substrate, where they are all connected by carbon islands. The zinc and cathode islands were then printed after that, a polyurethane pack was filled with a gel electrolyte and finally sealed.

The example printed stretchable, rechargeable IB zinc-silver oxide battery demonstrated good electrical and mechanical durability, as shown in FIGS. 14C and 14D, respectively, as the device can be easily wrapped around an index finger. The charge and discharge curves of the first cycle at 2 mA/cm are provided in FIG. 14E and followed by its cycling study. For this example, the complete battery design covers an area of ~8 $cm^2$ which demonstrated a total capacity of 1.6 mAh, with an effective areal capacity of 2.42 mAh/$cm^2$ for the 4.15 $mm^2$ area for 16 pairs of functional islands.

The example "island-bridge" designs for stretchable electronics integrate deterministic and intrinsic composite material design architectures through inexpensive, high-throughput screen-printing processes. The example stretchable devices were developed using the disclosed elastic composite inks that can be tailored with any conductive fillers and polymers specific to the application. The example mechanical deformation studies evaluating the serpentine designs and radial deformation of islands show the complexity of the island-bridge. For example, composite inks of varied compositions and materials exhibit unique strain-stress profiles. These example results highlight the complexity of the collective conformability of the printed "island-bridge". In some embodiments, the elastic conductive composite inks can include high-aspect ratio fillers, such as silver nanowires and carbon nanotubes. Other combinations of elastic polymer and conductive utility materials can provide other durable and high-performance epidermal electronics.

The low-cost and scalability of the example screen-printed stretchable electronics devices introduces a cost-effective alternative with the same ability to vary the design and components into a single, additive printing step. Furthermore, materials applicable to semiconductor processing are very limited, e.g., typically to one metal. The use of ink formulations allows any combination of conductive fillers and materials that vary in complexity across any technology. The development of a printed "island-bridge" may lead to a wide range of inexpensive stretchable electronics for a variety of applications. The serpentine designs are bound to the substrate but mechanical durability, which can be improved by freeing the design from the substrate. The method of synthesizing and tailoring inks for large-scale printing of stretchable devices holds great promise and study for conformal electronics.

Example embodiments of fabrication methods to produce the example elastic composite inks and example stretchable IB electronics devices used in the example implementations are described.

Example chemicals and reagents used in the example implementations include the following: Super-P Conductive Carbon Black (SP), toluene (Alfa Aesar), 200 proof Koptec (Decon Labs, King of Prussia, Pa.), Zn powder (Alfa Aesar), $Ag_2O$ powder (Alfa Aesar), $Bi_2O_3$ (Alfa Aesar), and universal mold release provided from Smooth On. KOH, LiOH, polyacrylic acid, silver flake (<10 micron), and SIS (14% styrene) were obtained from Sigma Aldrich, for example.

The example island-bridge stencil designs and devices were prepared as follows. The fabrication of screen printing electronics in an "island-bridge" configuration used an MPM-SPM semi-automatic screen printer (e.g., Speedline Technologies, Franklin, Mass.). The wide variety of serpentine and island designs were designed using CAD software, AutoCAD (e.g., Autodesk, San Rafael, Calif.). The design was then cut into a 300-micron thick, 12" by 12" stainless steel using a laser cutting (e.g., Metal Etch Services, San Marcos, Calif.). Due to improve cleaning of the stencil from dried ink inside the stencils features, for example, the stencil was coated with mold release spray (e.g., SmoothOn, Inc., PA).

The example composite inks used in the example implementations were formulated by dissolving 4 gram of SIS pellets in 10 mL with an analog vortex mixer (VMR) for 1 hour to make a viscous resin. The silver ink used for printing the example serpentine bridges was synthesized by mixing 1.2 grams of silver flake with 0.7 grams of the viscous resin. Additional 0.5 grams of 4 g of yttria stabilized zirconia grinding beads (e.g., 3 mm diameter, e.g., Inframat Advanced Materials) into the ink, then mixed using a dual asymmetric centrifugal mixer (e.g., Flacktek Speedmixer, DAC 150.1 KV-K) at 1800 rpm for 30 min. The elastic carbon ink was prepared by first dissolving 1.2 g of SIS pellets in 5 mL of 80% (v/v) toluene and 20% (v/v) ethanol with analog vortex mixer for 1 h. Then, 0.55 g of composite Super-P were mixed into the SIS solution in the dual asymmetric centrifugal mixer at 3000 rpm for 5 min. Due to the high shear shores generating heat from the mixing, for example, the ink is let to cool before adding 2 g of the yttria-stabilized zirconia grinding beads and additional 4 mL of the toluene/ethanol solution were added and underwent further mixing of 3000 rpm for 30 min. The battery inks and electrolytes were employed as previously described for the printed, stretchable battery. The example stretchable devices used a 26-micron thick polyurethane sheet (e.g., Delstar Technologies Inc. Middletown, Del.). The transfer any printed device to the epidermis used a water-soluble wave solder tape 5415 (e.g., 3M, St. Paul, Minn.) as the carrier. Printing directly on to a textile, the fabric was a polyurethane laminated (PUL) textile (e.g., Diaper Sewing Supplies, Fenton, Mo.).

The example stretching tests were conducted on a custom linear or biaxial stretching stage of a motorized linear stage and controller (e.g., A-LST0250A-E01 Stepper Motor and Controller, Zaber Technologies, Vancouver, Canada). The samples were programmed to constantly stretch at a speed of 0.08 mm s' from 0% to 100% and back to 0% as one cycle. The resistance was measured at 22 pt $s^{-1}$ using a digital multimeter (e.g., Agilent, Santa Clara, Calif.) during the ten cycles. The speed and length of the physical strain were programmed into a scripting software (e.g., Zaber console, Zaber Technologies, Vancouver, Canada).

The electrochemical tests were conducted at room temperature, for example. The electrochemical cycling tests were conducted with Arbin electrochemical cycler channels. Electrochemical cycling tests were conducted with 1 mA $cm^{-2}$ discharge current and charge current for the subsequent cycles. The discharge cut-off voltage was 0.8 V and the charge cut-off voltage was 2.3 V.

Example Applications

In some example embodiments in accordance with the present technology, the disclosed elastic composite materials can be used to produce conformal supercapacitor devices that includes the copolymer 101 and utility material 102 including a conductive material with high surface area (e.g. carbon, carbon nanotubes, graphene, etc.) that can store energy in an electric field.

In some example embodiments in accordance with the present technology, the disclosed elastic composite materials can be used to produce conformal energy harvester devices that includes the copolymer 101 and utility material 102 including piezoelectric and/or triboelectric fillers that can convert mechanical energy into electric energy. For example, a printed, stretchable triboelectric device can be used as an ultra-thin, flexible transducer for actuating signals or sensing noise, e.g., by having the example stretchable triboelectric device between to electrical contacts.

Also, for example, a conformal energy harvester device can include the copolymer 101 and utility material 102 including photovoltaic polymer or semiconductor, such that the device can convert light into electrical energy or vice versa to formulate a light emitting display.

In some example embodiments in accordance with the present technology, the disclosed elastic composite materials can be used to produce stretchable transistor devices that includes the copolymer 101 and utility material 102 including semiconductor material doped with impurities to synthesize a gate, gate dielectric, source, drain to form the transistor.

In some example embodiments in accordance with the present technology, the disclosed elastic composite materials can be used to produce a conformal color coat (e.g., paint) that includes the copolymer 101 and utility material 102 such as a colorant dye.

In some example embodiments in accordance with the present technology, the disclosed elastic composite materials can include a stretchable slurry for a silicon lithium ion battery (SLIB) anode, which includes the copolymer 101 and utility material 102 including silicon micro/nanoparticles, carbon additive, and a solvent. In some examples, the stretchable slurry can include 0.1%-20% wt of SIS, 80%-99.9% wt of an electrically conductive filler, and 10% wt additive material to formulate the slurry that is casted onto a conductive surface (e.g., copper foil), which can be set into a coin cell.

For example, the stretchable polymer forms an elastic network that can prevent pulverization, where the expansion of silicon upon lithiation can cause the fracture of an anode. Moreover, the example SLIB-type elastic composite material can improve the battery manufacturing or processing. For example, the use of the SLIB-type elastic composite material does not require water, unlike conventional anodes, in which water is a difficult solvent to disperse silicon, thereby simplifying slurry synthesis.

Figure 15:
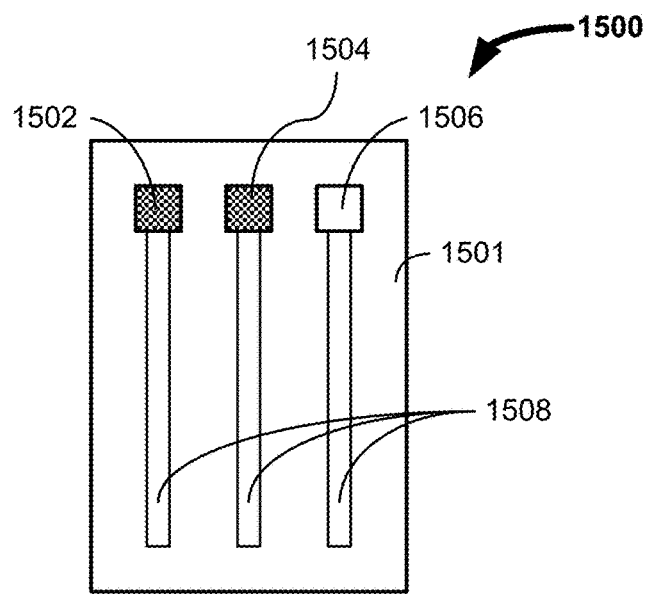
FIG. 15 shows a diagram of an example stretchable wearable sensor in accordance with the present technology.

FIG. 15 shows a diagram of an example stretchable wearable sensor 1500 in accordance with the present technology. The example stretchable sensor 1500 is shown in FIG. 15 as configured as a 3-electrode electrochemical sensor, and it is understood the example stretchable sensor 1500 can include fewer or greater electrodes, and can be configured for other sensor applications, such as electrophysiological sensing or other. The sensor 1500 includes a stretchable substrate 1501, e.g., including an elastic and electrically insulative material structured to conform to an outer surface of an object, such as skin. The sensor 1500 includes one or more electrodes, e.g., a working electrode 1504, counter electrode 1502 and reference electrode 1506, arranged over the stretchable substrate 1501. The one or more electrodes 1504, 1502 and/or 1506 include an example elastic composite material including an electrical conductor as the utility material 102, and the copolymer 101, e.g., SIS, configured to form a hyperelastic binder that creates contacts between particles of the electrical conductor within a network formed by the copolymer. In some examples for an electrochemical sensor, the working electrode 1504 and/or the counter electrode 1502 can include a functionalized coating with a catalytic layer for mediating an electrochemical reaction detectable by the stretchable sensor 1500.

Figure 16:
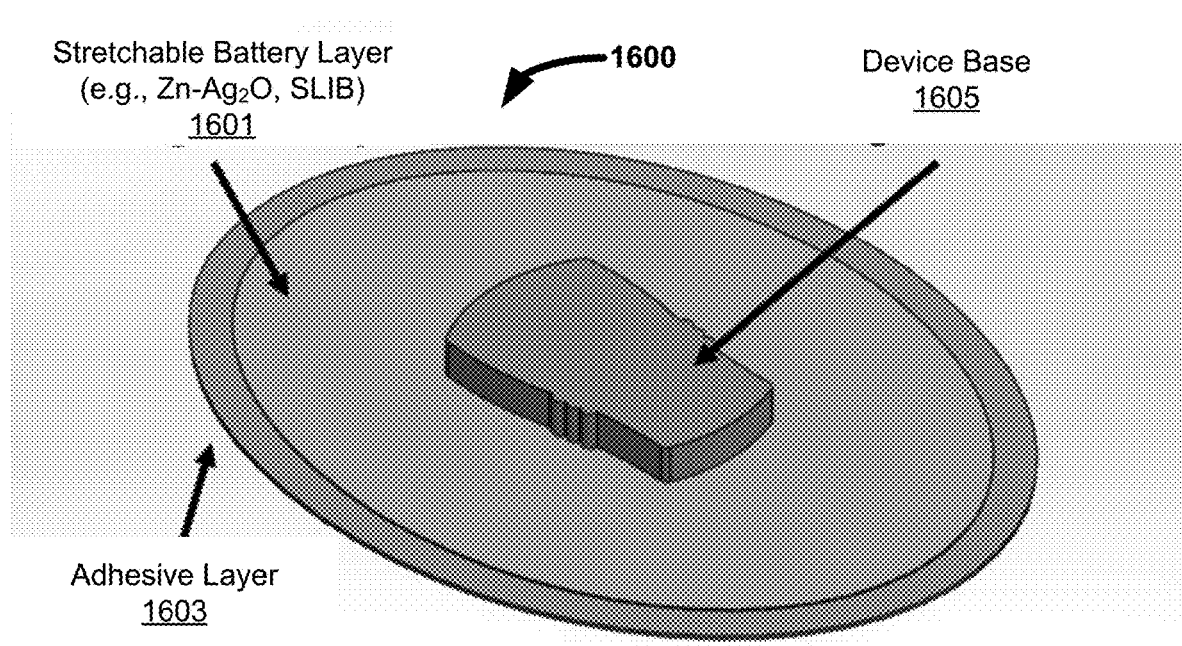
FIG. 16 shows a diagram of an example stretchable battery in accordance with the present technology.

FIG. 16 shows a diagram of an example stretchable battery 1600 configured as a stretchable battery layer 1601 attached to an adhesive 1603, which attaches to skin of a user or other surface of an object, and electrically coupled to a support base 1605 of a sensor device, e.g., such as an electronics unit and/or sensor unit. The stretchable battery 1601 can include any of the example embodiments of the stretchable battery in accordance with the present technology. In the example shown in FIG. 16, the stretchable battery layer 1601 can be integrated into the adhesive layer 1603 to form an adhesive patch, which can be applied to any surface, e.g., skin. The device base 1605 can include supportive electronics units, such as communication and power management, sensor electronics, etc., which can be a mounted dongle that attaches to the adhesive patch. The example stretchable device design would extremely reduce the bulk associated with conventional wearable sensors, and make the wearable device more compliant and therefore more comfortable to a user.

The examples above include various stretchable electronics devices and/or stretchable materials that can be made with the elastic composite material 100 that results in these different applications and use cases.

EXAMPLES

The following examples are illustrative of several embodiments in accordance with the present technology. Other exemplary embodiments of the present technology may be presented prior to the following listed examples, or after the following listed examples.

In some embodiments in accordance with the present technology (example 1), an elastic composite material includes a first material having a particular electrical, mechanical or optical property; and a multi-block copolymer configured to form a hyperelastic binder that creates contact between the first material and the multi-block copolymer, in which the elastic composite material is structured to stretch at least 500% in at least one direction of the material and to exhibit the particular electrical, mechanical or optical property imparted from the first material.

Example 2 includes the elastic composite material of example 1, in which the % wt of the first material is at least 60% and the % wt of the block copolymer is at most 40%.

Example 3 includes the elastic composite material of example 1, in which the % wt of the first material is at least 80% and the % wt of the block copolymer is at most 20%.

Example 4 includes the elastic composite material of example 1, in which the elastic composite material is structured to stretch at least 1000% in the at least one direction.

Example 5 includes the elastic composite material of example 1, in which the elastic composite material is structured to stretch at least 500% in at least two directions.

Example 6 includes the elastic composite material of example 5, in which the at least two directions are perpendicular.

Example 7 includes the elastic composite material of example 1, in which the multi-block copolymer includes polystyrene-polyisoprene-polystyrene (SIS).

Example 8 includes the elastic composite material of example 1, in which the multi-block copolymer includes a thermoplastic elastomer including styrene-ethylene/butylene-styrene (SEBS) block copolymer, styrene-ethylene/propylene-styrene (SEPS), or styrene-butadiene-styrene (SBS) block copolymer.

Example 9 includes the elastic composite material of example 1, in which the first material includes an electrical conductor, an electrical insulator, a dielectric, a ceramic, or a semiconductor.

Example 10 includes the elastic composite material of example 1, further including one or more additive materials.

Example 11 includes the elastic composite material of example 10, in which the % wt of the first material is at least 75%, the % wt of the block copolymer is at most 20%, and the % wt of the one or more additive materials is between 0.1% and 10%.

Example 12 includes the elastic composite material of example 10, in which the one or more additive materials includes a metal, a semiconductor, an organic polymer, an inorganic polymer, a ceramic, or a composite material.

Example 13 includes the elastic composite material of example 10, in which the one or more additive materials includes a nanoparticle, a nanowire, a nanofiber, or a nanoflake.

Example 14 includes the elastic composite material of example 10, in which the one or more additive materials includes a mineral oil, and the % wt of the mineral oil is between 1% and 2% of the elastic composite material.

Example 15 includes the elastic composite material of example 10, in which the one or more additive materials includes zinc oxide and bismuth oxide, and the % wt of the zinc oxide and bismuth oxide is each between 5% and 10%.

Example 16 includes the elastic composite material of example 10, in which the one or more additive materials includes a color agent.

Example 17 includes the elastic composite material of example 1, in which the multi-block copolymer forms a hyperelastic binder that creates contacts between particles of the first material within a network formed by the multi-block copolymer.

Example 18 includes the elastic composite material of example 1, in which the elastic composite material does not include a cross-linker for cross-linking strands of a polymer in the elastic composite material.

Example 19 includes the elastic composite material of example 1, in which the elastic composite material is in the form of a printable ink.

In some embodiments in accordance with the present technology (example 20), a method for producing a stretchable electronics device includes providing an electrically conductive ink that includes an elastic composite material including an electrically conductive material and a multi-block copolymer configured to form a hyperelastic binder that creates contact between the electrically conductive material and the multi-block copolymer; producing a first structure on a stretchable substrate by printing the electrically conductive ink through a first portion of a stencil structured to have a first design to form the geometry of the first structure, in which the stretchable substrate includes an elastic material structured to conform to an outer surface of an object; and producing a second structure on the stretchable substrate to produce a stretchable electronics article by printing the electrically conductive ink through the first portion of the stencil, or a second portion of the stencil structured to have a second design, or both the first portion and the second portion, to form the geometry of the second structure, in which the stretchable electronics article is able to stretch at least 500% in at least one direction and to exhibit electrical conductivity in the first structure while being stretched.

Example 21 includes the method of example 20, in which the stretchable substrate includes an electrically insulative material.

Example 22 includes the method of example 20, in which the multi-block copolymer of the elastic composite material includes poly styrene-polyisoprene-polystyrene (SIS).

Example 23 includes the method of example 20, in which the multi-block copolymer includes a thermoplastic elastomer including styrene-ethylene/butylene-styrene (SEBS) block copolymer, styrene-ethylene/propylene-styrene (SEPS), or styrene-butadiene-styrene (SBS) block copolymer.

Example 24 includes the method of example 20, in which the providing the electrically conductive ink includes providing a (i) first electrically conductive ink including a first elastic composite material including a first electrically conductive material and the multi-block copolymer, and (ii) a second electrically conductive ink including a second elastic composite material including a second electrically conductive material and the multi-block copolymer, the second electrically conductive material different than the first electrically conductive material, in which the producing the first structure includes printing the first electrically conductive ink, and in which the producing the second structure includes printing the second electrically conductive material.

Example 25 includes the method of example 24, in which the first structure forms a conductive underlayer of the stretchable electronics article, and the second structure forms an active layer that is printed over the conductive underlayer of the stretchable electronics device.

Example 26 includes the method of example 25, further including producing a third structure on the conductive underlayer to produce the stretchable electronics article by printing a third electrically conductive ink, which includes a third elastic composite material, through a third portion of the stencil structured to have a third design to form the geometry of the third structure, in which the third elastic composite material includes a third electrically conductive material different than the first and the second electrically conductive materials, and the multi-block copolymer.

Example 27 includes the method of example 26, in which the stretchable electronics article is a rechargeable Zn—Ag$_2$O battery, in which the first electrically conductive material includes carbon black, the second electrically conductive material includes zinc, and the third electrically conductive material includes silver oxide.

Example 28 includes the method of example 20, in which the stretchable substrate includes a textile.

Example 29 includes the method of example 28, in which the stretchable substrate includes a thermoplastic polyurethane sheet on the textile.

Example 30 includes the method of example 20, further including curing the printed electrically conductive ink on the stretchable substrate.

Example 31 includes the method of example 20, further including producing one or more outer features on the stretchable electronics article to electrically connect at least some of the structures or to provide contact structures that electrically connect to at least some of the structures.

Example 32 includes the method of example 20, further including forming a protective sheet over at least a portion of the produced stretchable electronics article.

Example 33 includes the method of example 20, in which the multi-block copolymer forms a hyperelastic binder that creates contacts between particles of the electrically conductive material within a network formed by the multi-block copolymer, and in which the provided electrically conductive ink does not include a cross-linker for cross-linking a polymer in the electrically conductive ink.

In some embodiments in accordance with the present technology (example 34), a stretchable electronics device includes a stretchable substrate including an elastic and electrically insulative material structured to conform to an outer surface of an object; and an electrode arranged over the stretchable substrate, in which the electrode is formed from an elastic composite material including an electrical conductor, and a multi-block copolymer configured to form a hyperelastic binder that creates contacts between particles of the electrical conductor within a network formed by the multi-block copolymer.

Example 35 includes the stretchable electronics device of example 34, in which the electrode is structured to stretch at least 500% in at least one direction and to exhibit electrical conductivity in the electrode.

Example 36 includes the stretchable electronics device of example 34, in which the electrode is structured to stretch at least 1000% in the at least one direction and to exhibit electrical conductivity in the electrode.

Example 37 includes the stretchable electronics device of example 34, in which the electrode is structured to stretch at least 500% in at least two directions, and the at least two directions are perpendicular.

Example 38 includes the stretchable electronics device of example 34, in which the multi-block copolymer of the elastic composite material includes polystyrene-polyisoprene-polystyrene (SIS).

Example 39 includes the stretchable electronics device of example 34, in which the % wt of the first material is at least 60% and the % wt of the block copolymer is at most 40%, or in which the % wt of the first material is at least 80% and the % wt of the block copolymer is at most 20%.

Example 40 includes the stretchable electronics device of example 34, further including a second electrode spaced from the first electrode, in which the second electrode is formed from a second elastic composite material including a second electrical conductor and the multi-block copolymer configured to form a hyperelastic binder that creates contacts between particles of the second electrical conductor within a network formed by the multi-block copolymer.

Example 41 includes the stretchable electronics device of example 40, in which the device includes a power storage device having an anode and a cathode corresponding to the electrode and the second electrode, respectively.

Example 42 includes the stretchable electronics device of example 41, in which the electrical conductor of the anode includes zinc and the second electrical conductor of the cathode includes silver oxide.

Example 43 includes the stretchable electronics device of example 40, further including a conductive layer attached to the stretchable substrate and configured under the first electrode, the second electrode, or both the first and second electrodes, in which the conductor layer is formed from a third elastic composite material including a third electrical conductor and the multi-block copolymer configured to form a hyperelastic binder that creates contacts between particles of the third electrical conductor within a network formed by the multi-block copolymer.

Example 44 includes the stretchable electronics device of example 43, in which the conductive layer includes carbon black.

Example 45 includes the stretchable electronics device of example 43, in which the device includes a power storage device having an anode and a cathode corresponding to the electrode and the second electrode, respectively, and the conductive layer is a current collector of the power storage device, in which the anode and the cathode are stacked vertically over the stretchable substrate with an electrolyte material in between the anode and the cathode.

Example 46 includes the stretchable electronics device of example 34, further including a second electrode spaced from the first electrode, in which the second electrode is formed from the elastic composite material.

Example 47 includes the stretchable electronics device of example 46, in which the device includes a sensor.

Example 48 includes the stretchable electronics device of example 34, further including an electrical contact on the stretchable substrate and electrically coupled to the electrode.

Example 49 includes the stretchable electronics device of example 34, further including a protective sheet over at least a portion of the stretchable electronics device.

Example 50 includes the stretchable electronics device of example 49, in which the protective sheet includes polyurethane.

In some embodiments in accordance with the present technology (example 51), a stretchable battery includes a stretchable substrate including an elastic and electrically insulative material structured to conform to an outer surface of an object; a current conductor layer attached to the stretchable substrate, in which the current conductor layer includes a first elastic composite material including a first electrical conductor and a multi-block copolymer configured to form a first hyperelastic binder that creates contacts between particles of the first electrical conductor within a network formed by the multi-block copolymer; an anode attached to the current conductor layer and arranged over the stretchable substrate, in which the anode includes a second elastic composite material including a second electrical conductor and the multi-block copolymer configured to form a second hyperelastic binder that creates contacts between particles of the second electrical conductor within a network formed by the multi-block copolymer; and a cathode arranged over the stretchable substrate, in which the cathode includes a third elastic composite material including a third electrical conductor and the multi-block copolymer configured to form a third hyperelastic binder that creates contacts between particles of the third electrical conductor within a network formed by the multi-block copolymer, in which the stretchable battery is operable to store energy while undergoing stretching.

Example 52 includes the stretchable battery of example 51, in which the current conductor layer, the anode and the cathode are structured to stretch at least 500% in at least one direction and concurrently exhibit electrical conductivity.

Example 53 includes the stretchable battery of example 51, in which the current conductor layer, the anode and the cathode are structured to stretch at least 1000% in at least one direction and concurrently exhibit electrical conductivity.

Example 54 includes the stretchable battery of example 51, in which the current conductor layer, the anode and the cathode are structured to stretch at least 500% in at least two directions and concurrently exhibit electrical conductivity, and the at least two directions are perpendicular.

Example 55 includes the stretchable battery of example 51, in which the multi-block copolymer of the elastic composite material includes polystyrene-polyisoprene-polystyrene (SIS).

Example 56 includes the stretchable battery of example 51, in which the first electrical conductor of the current collector layer includes carbon black, the second electrical conductor of the anode includes zinc, and the third electrical conductor of the cathode includes silver oxide.

Example 57 includes the stretchable battery of example 51, in which the % wt of at least one of the first, second or third electrical conductors is at least 60% and the % wt of the block copolymer is at most 40%.

Example 58 includes the stretchable battery of example 51, in which the anode and the cathode are stacked vertically over the stretchable substrate, the stretchable battery further including an electrolyte material arranged in between the anode and the cathode; and a second current collector layer attached to the cathode on a side opposite the electrolyte.

Example 59 includes the stretchable battery of example 58, further including a first electrical contact electrically coupled to the current collector layer and a second electrical contact electrically coupled to the second current collector layer.

Example 60 includes the stretchable battery of example 51, further including a protective sheet over at least a portion of the stretchable battery.

Example 61 includes the stretchable battery of example 60, in which the protective sheet includes polyurethane.

Example 62 includes the stretchable battery of example 51, in which the anode and the cathode are spaced horizontally over the stretchable substrate, the stretchable battery further including an electrolyte material arranged in between the anode and the cathode, in which the current collector layer includes two separate portions including a first portion attached to the anode and a second portion attached to the cathode on a side opposite the electrolyte.

Example 63 includes the stretchable battery of example 62, further including a first electrical contact electrically coupled to the current collector layer and a second electrical contact electrically coupled to the second current collector layer.

In some embodiments in accordance with the present technology (example 64), a stretchable battery including a stretchable substrate including an elastic and electrically insulative material structured to conform to an outer surface of an object; a first electrical interconnection structure and a second electrical interconnection structure each attached to the stretchable substrate and having a periodic curved horseshoe geometry configured to connect unit cell regions positioned on the electrical interconnection structure, in which the first and the second interconnection structures include a first elastic composite material including a first electrical conductor and a multi-block copolymer configured to form a first hyperelastic binder that creates contacts between particles of the first electrical conductor within a network formed by the multi-block copolymer; a plurality of current conductor components attached to the electrical interconnection structure at the unit cell regions, in which the current conductor layer includes a second elastic composite material including a second electrical conductor and a multi-block copolymer configured to form a second hyperelastic binder that creates contacts between particles of the second electrical conductor within a network formed by the multi-block copolymer; a plurality of anodes attached to the current conductor component over the unit cell regions of the first electrical interconnection structure, in which the anodes include a third elastic composite material including a third electrical conductor and the multi-block copolymer configured to form a third hyperelastic binder that creates contacts between particles of the third electrical conductor within a network formed by the multi-block copolymer; and a plurality of cathodes attached to the current conductor component over the unit cell regions of the second electrical interconnection structure, in which the cathodes include a fourth elastic composite material including a fourth electrical conductor and the multi-block copolymer configured to form a fourth hyperelastic binder that creates contacts between particles of the fourth electrical conductor within a network formed by the multi-block copolymer, in which the stretchable battery is operable to store energy while undergoing stretching.

Example 65 includes the stretchable battery of example 64, in which the first and second electrical interconnection structures, the current conductor component, the anode and the cathode are structured to stretch at least 500% in at least one direction and concurrently exhibit electrical conductivity.

Example 66 includes the stretchable battery of example 64, in which the first and second electrical interconnection structures, the current conductor component, the anode and the cathode are structured to stretch at least 1000% in at least one direction and concurrently exhibit electrical conductivity.

Example 67 includes the stretchable battery of example 64, in which the first and second electrical interconnection structures, the current conductor component, the anode and the cathode are structured to stretch at least 500% in at least two directions and concurrently exhibit electrical conductivity, and the at least two directions are perpendicular.

Example 68 includes the stretchable battery of example 64, in which the multi-block copolymer of the elastic composite material includes polystyrene-polyisoprene-polystyrene (SIS).

Example 69 includes the stretchable battery of example 64, in which the first electrical conductor of the electrical interconnection structure includes silver, the second electrical conductor of the current collector component includes carbon black, the third electrical conductor of the anode includes zinc, and the fourth electrical conductor of the cathode includes silver oxide.

Example 70 includes the stretchable battery of example 64, in which the unit cell regions have an area of 5 $mm^2$ or less.

Example 71 includes the stretchable battery of example 64, in which the first and second electrical interconnection structures each include four branches including each having four of the unit cell regions such that the stretchable battery includes 16 anode-cathode pairs, in which the stretchable battery includes a total footprint of 8 $cm^2$ or less.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A stretchable electronics device, comprising:
a stretchable substrate including an elastic and electrically insulative material structured to conform to an outer surface of an object;
an electrode arranged over the stretchable substrate, wherein the electrode is formed from an elastic composite material comprising an electrical conductor, and a multi-block copolymer configured to form a hyperelastic binder that creates contacts between particles of the electrical conductor within a network formed by the multi-block copolymer;
a second electrode spaced from the first electrode, wherein the second electrode is formed from a second elastic composite material comprising a second electrical conductor and the multi-block copolymer configured to form a hyperelastic binder that creates contacts between particles of the second electrical conductor within a network formed by the multi-block copolymer; and
a conductive layer attached to the stretchable substrate and configured under the first electrode, the second electrode, or both the first and second electrodes, wherein the conductor layer is formed from a third elastic composite material comprising a third electrical conductor and the multi-block copolymer configured to form a hyperelastic binder that creates contacts between particles of the third electrical conductor within a network formed by the multi-block copolymer.

2. The stretchable electronics device of claim 1, wherein the electrode is structured to stretch at least 500% in at least one direction and to exhibit electrical conductivity in the electrode.

3. The stretchable electronics device of claim 1, wherein the electrode is structured to stretch at least 1000% in the at least one direction and to exhibit electrical conductivity in the electrode.

4. The stretchable electronics device of claim 1, wherein the electrode is structured to stretch at least 500% in at least two directions, and the at least two directions are perpendicular.

5. The stretchable electronics device of clam 1, wherein the multi-block copolymer of the elastic composite material includes poly styrene-polyisoprene-poly styrene (SIS).

6. The stretchable electronics device of claim 1, wherein the %wt of the elastic composite material is at least 60% and the %wt of the block copolymer is at most 40%, or
wherein the %wt of the elastic composite material is at least 80% and the %wt of the block copolymer is at most 20%.

7. The stretchable electronics device of clam 1, wherein the device includes a power storage device having an anode and a cathode corresponding to the electrode and the second electrode, respectively.

8. The stretchable electronics device of claim 7, wherein the electrical conductor of the anode includes zinc and the second electrical conductor of the cathode includes silver oxide.

9. The stretchable electronics device of claim 1, wherein the conductive layer includes carbon black.

10. The stretchable electronics device of claim 1, wherein the device includes a power storage device having an anode and a cathode corresponding to the electrode and the second electrode, respectively, and the conductive layer is a current collector of the power storage device, wherein the anode and the cathode are stacked vertically over the stretchable substrate with an electrolyte material in between the anode and the cathode.

11. The stretchable electronics device of claim 1, further comprising:
a second electrode spaced from the first electrode, wherein the second electrode is formed from the elastic composite material.

12. The stretchable electronics device of claim 11, wherein the device includes a sensor.

13. The stretchable electronics device of claim 1, further comprising:
an electrical contact on the stretchable substrate and electrically coupled to the electrode.

14. The stretchable electronics device of claim 1, further comprising:
a protective sheet over at least a portion of the stretchable electronics device.

15. The stretchable electronics device of claim 14, wherein the protective sheet includes polyurethane.

16. A stretchable electronics device, comprising:
a stretchable substrate including an elastic and electrically insulative material structured to conform to an outer surface of an object; and
an electrode arranged over the stretchable substrate, wherein the electrode is formed from an elastic composite material comprising an electrical conductor, and a multi-block copolymer configured to form a hyperelastic binder that creates contacts between particles of the electrical conductor within a network formed by the multi-block copolymer,
wherein the multi-block copolymer of the elastic composite material includes polystyrene-polyisoprene-polystyrene (SIS).

17. The stretchable electronics device of claim 16, wherein:
the %wt of the elastic composite material is at least 60% and the %wt of the block copolymer is at most 40%, or
the %wt of the elastic composite material is at least 80% and the %wt of the block copolymer is at most 20%.

18. The stretchable electronics device of claim 16, wherein the electrode is structured to stretch at least 500% in at least one direction and to exhibit electrical conductivity in the electrode.

19. The stretchable electronics device of claim 16, wherein the electrode is structured to stretch at least 500% in at least two directions, and the at least two directions are perpendicular.

20. The stretchable electronics device of clam 16, wherein the device includes a power storage device having an anode and a cathode corresponding to the electrode and the second electrode, respectively.

* * * * *